United States Patent [19]
Er et al.

[11] Patent Number: 5,974,341
[45] Date of Patent: Oct. 26, 1999

[54] METHOD AND APPARATUS FOR DETECTING AND DISPLAYING DIAGNOSTIC INFORMATION IN CONJUNCTION WITH INTRACARDIAC ELECTROGRAMS AND SURFACE ELECTROCARDIOGRAMS

[75] Inventors: Siew Bee Er, Newhall; Melinda A. Endaya, Granada Hills, both of Calif.

[73] Assignee: Pacesetter, Inc., Sylmar, Calif.

[21] Appl. No.: 08/995,784

[22] Filed: Dec. 22, 1997

[51] Int. Cl.$^6$ .................................................. A61N 1/37
[52] U.S. Cl. .......................................................... 607/31
[58] Field of Search ................................ 607/27, 28, 31; 600/510

[56] References Cited

U.S. PATENT DOCUMENTS

| | | |
|---|---|---|
| 4,791,936 | 12/1988 | Snell et al. . |
| 4,809,697 | 3/1989 | Causey et al. . |
| 4,940,052 | 7/1990 | Mann et al. . |
| 4,944,298 | 7/1990 | Sholder . |
| 4,944,299 | 7/1990 | Silvian . |
| 5,292,341 | 3/1994 | Snell et al. . |
| 5,423,867 | 6/1995 | Poore et al. . |
| 5,431,691 | 7/1995 | Snell et al. . |
| 5,620,473 | 4/1997 | Poore . |
| 5,653,737 | 8/1997 | van Lake . |

Primary Examiner—William E. Kamm

[57] ABSTRACT

A pacemaker generates and transmits real-time intracardiac electrogram signals to an external display device for display thereon. Simultaneously, the pacemaker senses a variety of events occurring either within the heart tissue or within the pacemaker itself and transmits signals representative of those events for display, using appropriate marker icons, along with the intracardiac electrograms. In this manner, a physician viewing the intracardiac electrograms is simultaneously apprised of the various events. In one example, events displayed along with the intracardiac electrograms include the detection of atrial and ventricular events occurring within the heart during a non-absolute refractory period following generation of a stimulation signal. Other examples of events displayed along with the intracardiac electrograms include operations triggered within the pacemaker as a result of the condition of the patient, such as an auto-mode switching event, or operations triggered within the pacemaker as a result of the condition of the pacemaker itself, such as a battery test operation. Still other examples of events include pacemaker programming operations triggered using a remote programming device by a physician. Such events include an electrophysiological artificially-induced arrhythmia operation. In the described example, the external display device also presents surface electrocardiograms along with the intracardiac electrograms and the event marker icons.

34 Claims, 12 Drawing Sheets

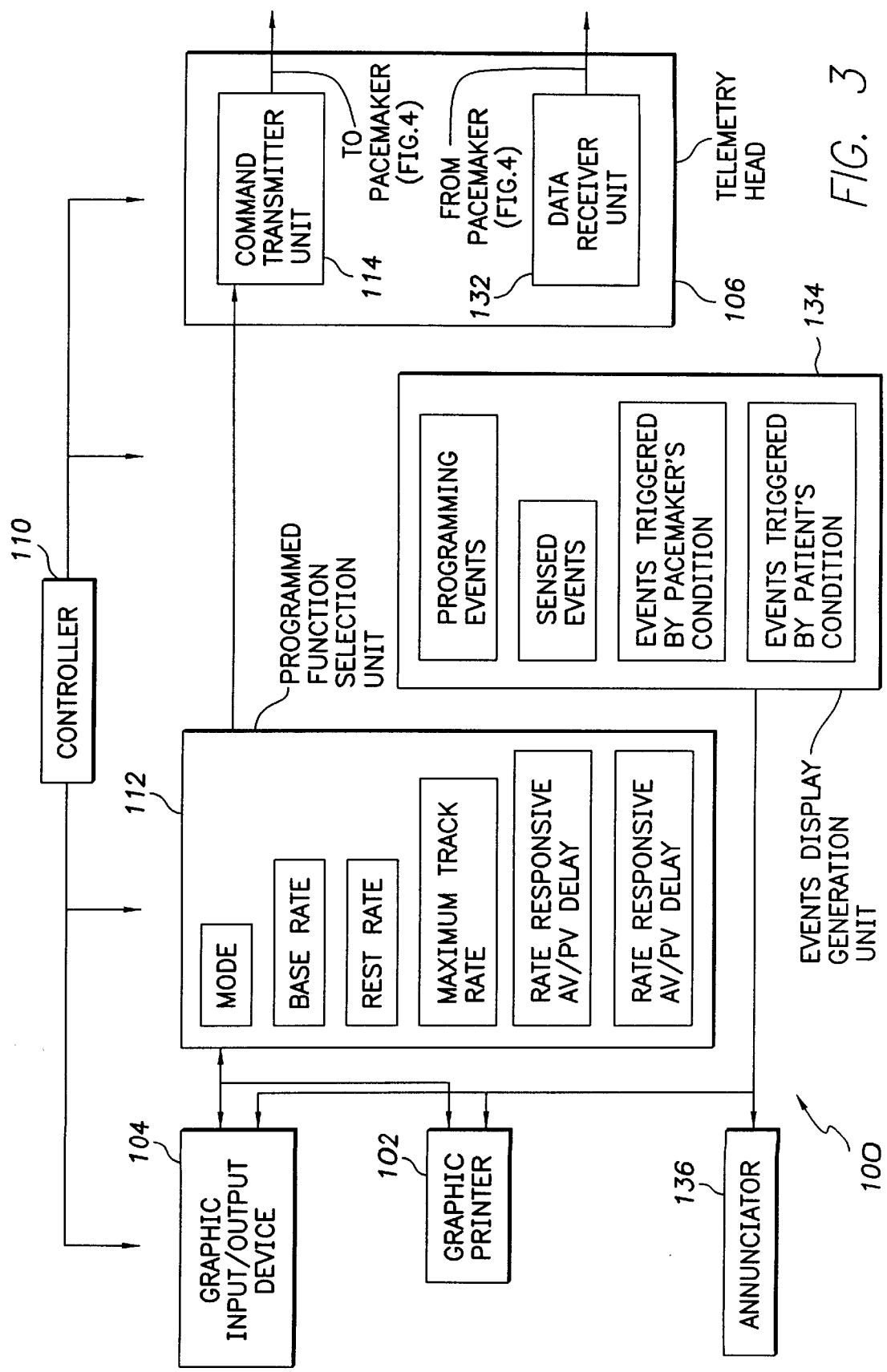

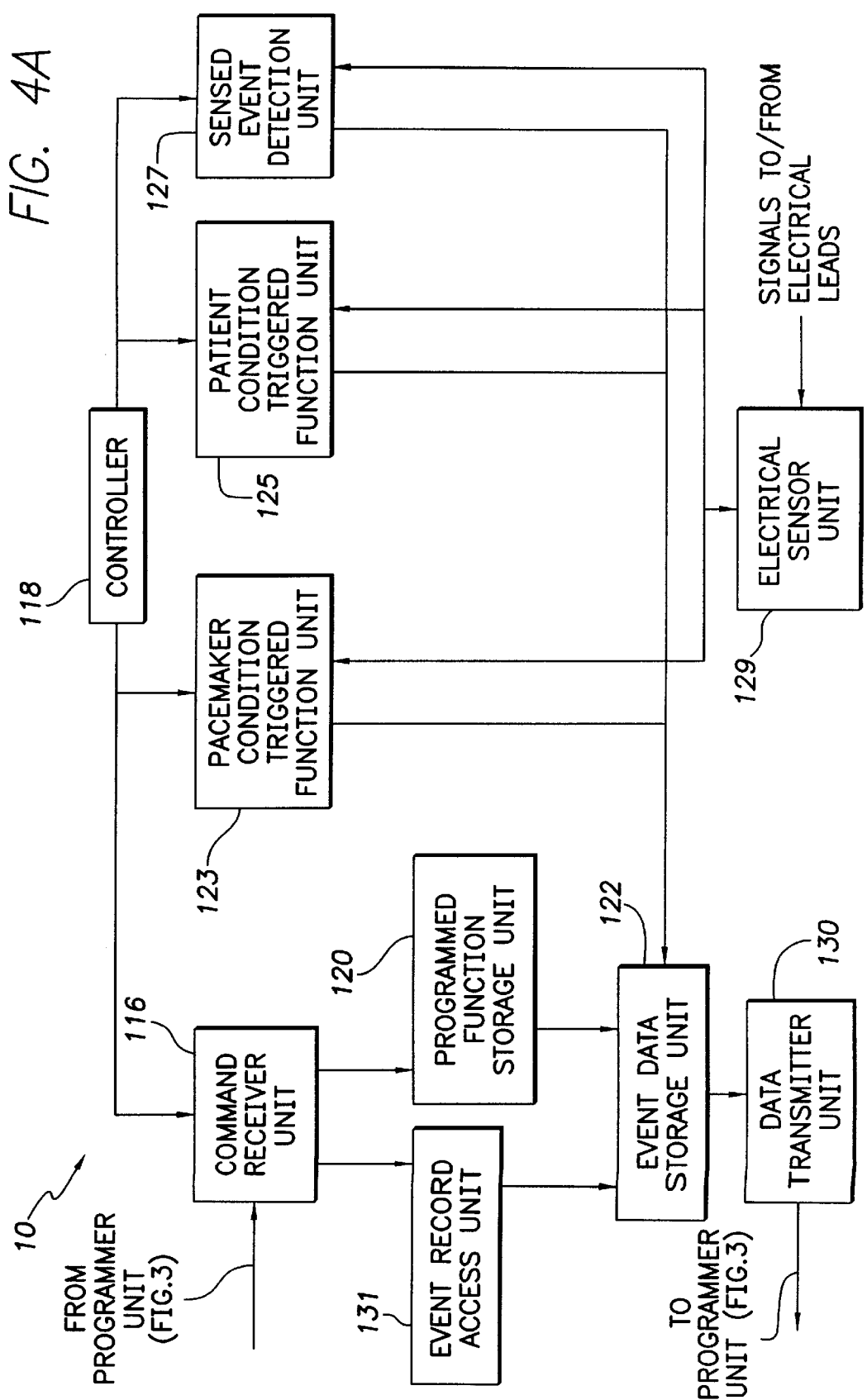

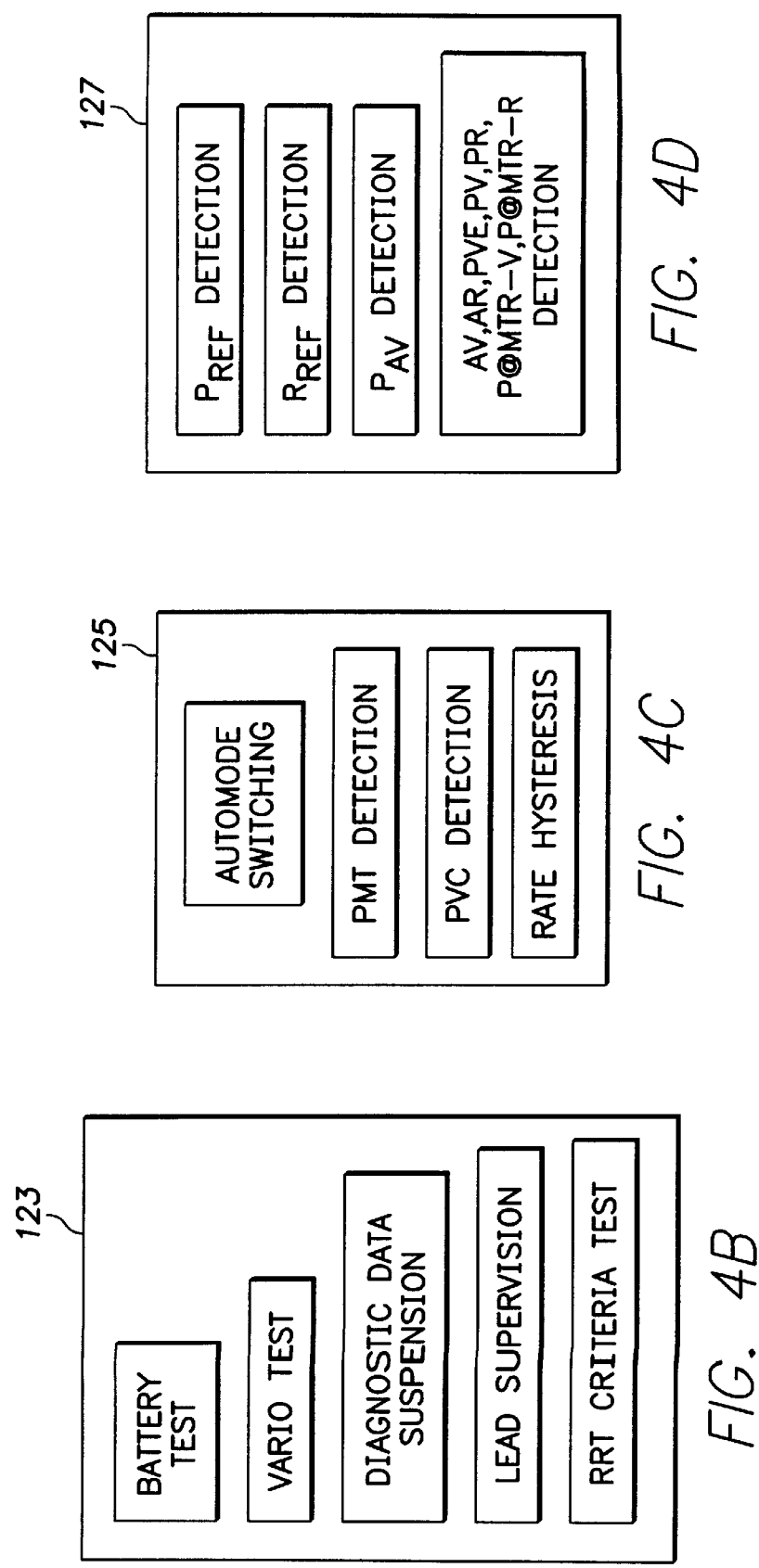

Jul 22 1995 4:14 pm
MODEL:         SERIAL:

PATIENT: JOHN BROWN / 123-456-7890

PHYSICIAN: VALLEY VIEW HOSPITAL / DR. GREEN

| Parameter | Programmed | Temporarily Programmed | |
|---|---|---|---|
| Mode | VVIR | DDDR | |
| Rate | 60 | 70 | ppm |
| Sensor | PASSIVE | PASSIVE | |
| AV Delay | 125 | 150 | msec |
| Vent. Pulse Config. | UNIPOLAR | BIPOLAR | |
| Vent. Sense Config. | UNIPOLAR TIP | BIPOLAR | |
| Atrial Pulse Config. | UNIPOLAR | BIPOLAR | |
| Atrial Sense Config. | UNIPOLAR TIP | BIPOLAR | |

ECG/IEGM PARAMETERS

| | |
|---|---|
| Surface ECG Gain | 1.0 mv/div |
| Surface ECG Filter | ON |
| Intracardiac EGM Gain | 2.5 mv/div |
| Sweep Speed | 25.0 mm/sec |

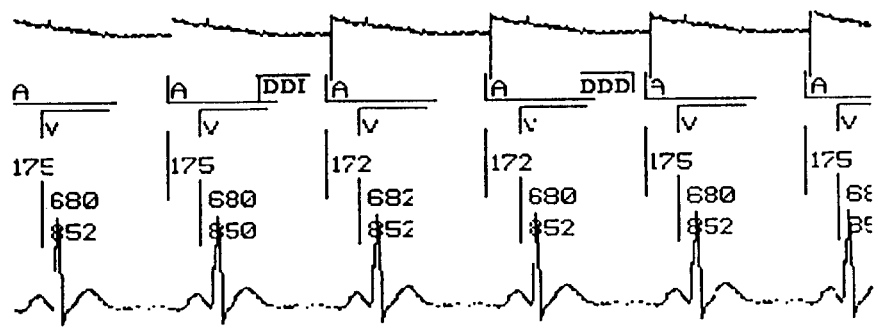

Surface ECG 1.0 SEC

FIG. 13

METHOD AND APPARATUS FOR DETECTING AND DISPLAYING DIAGNOSTIC INFORMATION IN CONJUNCTION WITH INTRACARDIAC ELECTROGRAMS AND SURFACE ELECTROCARDIOGRAMS

FIELD OF THE INVENTION

The invention generally relates to implantable medical devices and to external programmer devices used in connection therewith and in particular to methods and apparatus for processing and displaying diagnostic information detected by the implantable medical device in conjunction with displays of intracardiac electrograms (IEGM's) and surface electrocardiograms (ECG's).

BACKGROUND OF THE INVENTION

A wide range of implantable medical devices are provided for surgical implantation into humans or animals. One common example is the cardiac pacemaker. Another is the implantable cardioverter defibrillator. Other examples include devices for stimulating or sensing portions of the brain, spinal cord, muscles, bones, nerves, glands or other body organs or tissues.

Implantable medical devices, particularly pacemakers, are often configured to be used in conjunction with an external programmer device which allows a physician to display information sensed by the device. For a pacemaker, for example, the external programmer device may operate to display electrical cardiac signals detected by the pacemaker in the form of IEGM's and ECG's. An IEGM is a graphic depiction of electrical signals emitted by active cardiac tissue as detected by electrodes placed on or in the heart. An ECG is also a graphic depiction of the electrical signals emitted by active cardiac tissue but is detected using electrodes placed on the body surface rather than in or on the heart itself.

One example of an external programmer that displays IEGM's and ECG's is an analyzer-programmer system (APS) identified as the APS II system which is provided by Pacesetter Inc. of Sylmar, Calif. More specifically, the APS II system displays IEGM's and surface ECG's in conjunction with icons representative of paced and sensed atrial and ventricular events such as atrial stimulus, ventricular stimulus, atrial activity outside atrial refractory/blanking period, ventricular activity outside ventricular refractory/blanking period, and the length of atrial refractory period. The APS II system also displays variable length horizontal lines representative of the length of the atrial and ventricular refractory periods and also displays numerical values indicative of measured intervals between the atrial and ventricular events. Further information regarding the detection and display of IEGM signals may be found in U.S. Pat. No. 5,620,473 to John W. Poore entitled "Calibration System for Pacemaker-Generated Intracardiac Electrogram" which provides for the display and calibration of IEGM signals. U.S. Pat. No. 5,620,473 is also incorporated by reference herein.

Other components of the APS II system of Pacesetter Inc. operate to allow a physician to program the operation of the pacemaker to, for example, control the specific parameters by which the pacemaker senses the IEGM signals and the manner by which the pacemaker detects arrhythmia conditions within the heart and responds thereto. For example, the APS II system allows the physician to specify the sensitivity with which the pacemaker senses electrical signals within the heart and to further specify the amount of electrical energy to be employed for pacing the heart in circumstances where expected heart signals are not sensed. Still other components of the APS II system operate to display a variety of diagnostic information received from the pacemaker. More specifically, the APS II system displays the different types of diagnostic information set forth in TABLE I.

TABLE I

| EVENT NAME | EVENT TYPE |
| --- | --- |
| AV | A-pulse followed by a V-pulse |
| AR | A-pulse followed by an R-wave |
| PVE | Premature ventricular event |
| PV | P-wave followed by a V-pulse |
| PR | P-wave followed by an R-wave |
| P@MTR-V | P-wave at maximum tracking rate followed by a V-pulse |
| P@MTR-R | P-wave at maximum tracking rate followed by a R-wave |
| MAGNET | Magnet placed over the implanted device--either singly or in combination with an external telemetry system |

U.S. Pat. No. 5,431,691 to Snell et al. entitled "Method and System for Recording and Displaying a Sequential Series of Pacing Events" provides a detailed description of the operation of the APS II system of Pacesetter Inc. including a description of the processing and displaying of the diagnostic information set forth in TABLE I. In particular, the Snell et al. patent describes a technique whereby the pacemaker processes and records diagnostic data in the form of "event records" which allow the data to be efficiently stored within the pacemaker, transmitted to the APS II system, and displayed. U.S. Pat. No. 5,431,691 to Snell et al. is incorporated by reference herein.

As can be seen from TABLE I, the events processed by the APS II system are primarily events sensed within the heart of the patient. Event records containing information pertaining to those events are recorded within the pacemaker for subsequent transmission to the external programmer for display thereon in a variety of formats including event record displays, event bar graphs, rate bar graphs, rate time graphs, and event time graphs, each under the control of the physician operating the external programmer. More specifically, the event record display presents the various detected events of TABLE I and the corresponding pacing rate with respect to the time of the occurrence of the event. For periods of time while the pacemaker is in a dual-chamber mode (such as DDD, DDI etc.), the events presented include PV, PR, AV (or V when the mode is VDDR or VDD), AR and PVC (premature ventricular contraction). For periods of time while the pacemaker is in a single-chamber mode (such as VVI, AAI etc.), the events are presented merely as paced or sensed. The event bar graph presents a histogram of different event types listing the total number of counts of each event type for a selected period of time. The event time graph presents histograms of event types vs. time of event occurrence. The rate bar graph presents histograms of sensed and paced events vs. their rate. The rate time graph presents histograms of rates vs. times. Further information regarding the different displays may be found in the Snell et al. patent.

As can be appreciated, a wide range of useful information, particularly directed to events sensed within the heart, is thereby provided to assist the physician in rendering a diagnosis as to any arrhythmia or other condition the patient may exhibit or to assist the physician in making choices as to adjusting various parameters by which the pacemaker monitors and paces the heart. The information is displayed in a variety of convenient graphical formats to help the physician visualize the information quickly and easily to facilitate prompt and accurate diagnoses.

The parent application referenced above describes various improvements to the APS II system. For example, the parent application describes improvements wherein the system records and displays numerous additional types of diagnostic data including data pertaining to 1) operational events triggered within the pacemaker as a result of the condition of the patient (such as automode switching events) and 2) operational events triggered within the pacemaker as a result of the condition of the pacemaker itself (such as battery tests or lead fault detection tests). The additional diagnostic data is displayed as part of one or more of the aforementioned event record displays, event bar graphs, rate bar graphs, rate time graphs, and event time graphs.

Although the system described in the parent application, which displays the additional diagnostic information in conjunction with event records, represents an improvement over the ASP II system, further room for improvement remains. In particular, it would be desirable to also display at least some of the additional types of event record diagnostic information in conjunction with the aforementioned IEGM and surface ECG displays to allow the physician to view the additional event record diagnostic information while simultaneously viewing IEGM's or ECG's and it is primarily to that end that the present invention is directed.

SUMMARY OF THE INVENTION

In accordance with one aspect of the invention, a method is provided for detecting and displaying information using a system having an implantable medical device and an external display device wherein the implantable medical device is capable of generating a stimulation signal within heart tissue connected to the implantable medical device and is capable of sensing electrical signals and events occurring within the heart tissue. The information displayed includes IEGM's along with markers representative of electrical events detected during a non-absolute refractory period following generation of a stimulation signal with the heart tissue. The method includes the steps of detecting IEGM signals representative of the electrical activity of the heart tissue connected to the implantable medical device; generating a stimulation signal within the heart tissue; and detecting electrical events occurring within the heart tissue during a non-absolute refractory period following generation of the stimulation signal. The method includes the additional steps of transmitting, from the implantable medical device to the external display device, the IEGM signals and the signals representative of the events detected during the non-absolute refractory period; receiving the transmitted signals at the external display device; and, in response to the received signals, graphically displaying the IEGM signals on the external display device along with icons representative of the detected events.

In one specific example, where the implantable medical device is a pacemaker, the events detected during the non-absolute refractory period following generation of the stimulation signal include the detection of atrial activity and the detection of ventricular activity. The external display device is a computer display screen or a computer print-out device. The external device additionally displays surface ECG's. The IEGM's and ECG's generated by the external display device are presented substantially in real-time.

In accordance with another aspect of the invention, a method is provided for detecting and displaying information using an implantable medical device, an external display device and a remote programming device wherein the information displayed includes IEGM's along with markers representative of programming operations that had been triggered within the implantable medical device as a result of programming signals received from the remote programming device. The method includes the steps of receiving programming signals from the remote programming device using the implantable medical device; triggering operations within the implantable medical device in response to the received programming signals; and detecting IEGM signals representative of the electrical activity of the heart tissue. The method also includes the steps of transmitting, from the implantable medical device to the external display device, the IEGM signals along with signals representative of the operations triggered within the implantable medical device; receiving the transmitted signals at the external display device; and, in response to the received signals, graphically displaying the IEGM signals on the external display device along with icons representative of the programming operations that had been triggered within the implantable medical device.

In one specific example, wherein the implantable medical device includes a pacemaker, the operations triggered within the pacemaker include artificially induced arrhythmia (hereinafter also referred to as electrophysiological (EP) Lab). The remote programming device may be a magnet operated by a physician or may be part of a programmer unit operated by a physician. As before, the external display device may additionally display surface ECG's, and the IEGM's and ECG's generated by the external display device are presented substantially in real-time.

In accordance with yet another aspect of the invention, a method is provided for detecting and displaying information using an implantable medical device and an external display device wherein the information displayed includes IEGM's along with markers representative of operations that had been triggered within the implantable medical device by conditions sensed by the implantable medical device. The method comprises the steps of sensing conditions using the implantable medical device; triggering operations within the implantable medical device in response to the sensed conditions; and detecting IEGM signals representative of the electrical activity of the heart tissue. The method also includes the steps of transmitting, from the implantable medical device to the external display device, the IEGM signals along with signals representative of operations triggered within the implantable medical device in response to the sensed conditions; receiving the transmitted signals at the external display device; and, in response to the received signals, graphically displaying the IEGM signals on the external display device along with icons representative of the operations that had been triggered within the implantable medical device.

In one example, wherein the implantable medical device includes a pacemaker, the pacemaker is capable of sensing conditions of the heart of a patient in which the pacemaker is implanted. The aforementioned operations are triggered based upon the sensed conditions of the heart and include operations such as automatic pacemaker mode switching (i.e. automode switching), pacemaker mediated tachycardia (PMT) detection, and premature ventricular contraction (PVC) detection, rate hysteresis search and AV/PV hysteresis search.

Also in the example wherein the implantable medical device again includes a pacemaker, the pacemaker is additionally capable of sensing performance parameters representative of its own performance. The operations triggered within the pacemaker include operations such as a battery test and a lead fault detection test triggered by the sensed performance parameters. As before, the external display device may additionally display surface ECG's, and the IEGM's and ECG's generated by the external display device are presented substantially in real-time.

Hence, with the invention, various methods are provided for graphically displaying a wide variety of diagnostic information in combination with IEGM and ECG displays not heretofore presented in a single convenient display to the physician, to thereby assist the physician in making quick and informed decisions regarding, for example, the patient's condition or the condition of the implantable medical device.

Other objects and advantages of the invention are achieved as well. Apparatus embodiments of the invention are also provided.

BRIEF DESCRIPTION OF THE DRAWINGS

FIG. 3 is block diagram of pertinent components of a first embodiment of the external programmer of FIG. 2 for use in generating and displaying enhanced event markers and event control records received from the implantable pacemaker of FIG. 1.

FIG. 4 is block diagram of pertinent components of the first embodiment of the implantable pacemaker of FIG. 1 for use in generating the enhanced event markers and event control records for display using the external programmer of FIG. 3.

FIG. 13 is an exemplary IEGM printout generated the external programmer device of FIG. 8.

DETAILED DESCRIPTION OF THE INVENTION

Figure 1:
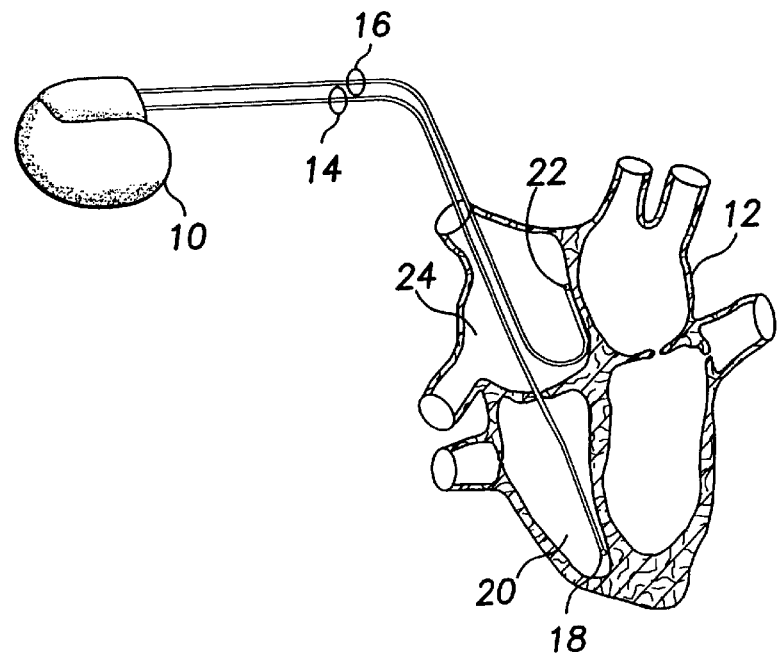
FIG. 1 shows an implantable pacemaker coupled to a heart via a pair of electrical leads.

The invention relates to improved techniques for providing information to a physician regarding the events detected by an implantable medical device. The invention will be described primarily with reference to a pacemaker used in conjunction with an external programmer device, but principles of the invention are applicable to other implantable medical devices and other external devices as well.

The Figures illustrate a pacemaker/programmer system having a pacemaker for implantation into a patient and an external programmer for programming the operation of the pacemaker and for processing and displaying information received from the pacemaker regarding the condition of a patient in which the pacemaker is implanted and regarding the condition of the pacemaker itself. The information is stored within the pacemaker in an event record format which efficiently allows a wide variety of types of information to be stored, along with the date and time at which the information was stored, within the pacemaker for subsequent transmission to the external programmer. The external programmer includes processing units for receiving event records transmitted by the pacemaker and for generating a wide variety of graphical displays of the information contained within the event records under the control of the physician operating the external programmer.

The Snell et al. patent, incorporated by reference above, describes a predecessor pacemaker/programmer system which also operates to generate, store and process certain types of information within event records to generate certain displays based upon the information contained within the event records. The pacemaker/programmer system of the present invention operates to generate, store and process many additional types of information within event records to generate enhanced displays based upon the information contained within the event records. In the following descriptions, for the sake of clarity in describing pertinent features of the enhanced pacemaker/programmer system, many details of the operation of the overall pacemaker/programmer system provided in the Snell et al. patent are not repeated herein. Additional operational details pertaining to either the pacemaker, programmer or both may be found in the following patents, each of which is also incorporated by reference herein: U.S. Pat. No. 4,940,052 entitled "Microprocessor controlled rate-responsive pacemaker having automatic rate response threshold adjustment"; U.S. Pat. No. 4,809,697 entitled "Interactive Programming And Diagnostic System For Use With Implantable Pacemaker"; U.S. Pat. No. 4,791,936 entitled "Apparatus For Interpreting And Displaying Cardiac Events Of A Heart Connected To A Cardiac Pacing Means"; U.S. Pat. No. 5,309,919 entitled "Method And System For Recording, Reporting, And Displaying The Distribution Of Pacing Events Over Time And For Using Same To Optimize Programming"; U.S. Pat. No. 4,944,299 entitled "High Speed Digital Telemetry System For Implantable Device"; U.S. Pat. No. 5,292,341 entitled "Method And System For Determining And Automatically Adjusting The Sensor Parameters Of A Rate-Responsive Pacemaker"; U.S. Pat. No. 5,423,867 entitled "Rate-Responsive Pacemaker Having Automatic Sensor Threshold With Programmable Offset"; and U.S. Pat. No. 4,944,298 entitled "Atrial Rate Based Programmable Pacemaker With Automatic Mode Switching Means".

First Exemplary Embodiment

FIG. 1 illustrates an implantable pacemaker 10 coupled to a heart 12 by way of a ventricular lead 14 and an atrial lead 16. Ventricular lead 14 includes an electrode 18 positioned in the right ventricle 20 of the heart and atrial lead includes an electrode 22 positioned in the right atrium 24 of the heart.

Various internal components of the pacemaker operate to sense the electrical activity of the heart, such as the presence of P-waves and R-waves, using electrodes 18 and 22 and to selectively stimulate the heart in response to events sensed within the heart by conducting electrical stimulation pulses to the heart using the electrodes. The pacemaker may be configured to operate in either a single-chamber mode or a dual-chamber mode. Certain of the events sensed within the heart are recorded by internal components of the pacemaker within event records for subsequent transmission to an external programmer (FIG. 2) for display thereon in a graphical format. TABLE II provides a list of sensed events stored in pacemaker 10 of FIG. 1 using event records while the pacemaker is operating is the dual-chambered mode. Notably, the events listed in TABLE II include three events $P_{REF}$ detected, $R_{REF}$ detected and $P_{AV}$ detected occurring during refractory periods following the generation of stimulation signals.

TABLE II

| SENSED EVENT NAME | SENSED EVENT TYPE |
|---|---|
| AV | A-Pulse Followed By A V-Pulse Detected |
| AR | A-Pulse Followed By An R-Wave Detected |
| PVE | Premature Ventricular Event Detected |
| PV | P-Wave Followed By A V-Pulse Detected |
| PR | P-Wave Followed By An R-Wave Detected |
| P@MTR-V | P-Wave At Maximum Tracking Rate Followed By A V-Pulse Detected |
| P@MTR-R | P-Wave At Maximum Tracking Rate Followed By A R-Wave Detected |
| $P_{REF}$ | P-Wave Detected During A Relative Post-Ventricular Atrial Refractory Period (PVARP) Not Followed By A Ventricular Pulse |
| $R_{REF}$ | R-Wave Detected During A Relative Ventricular Refractory Period |
| $P_{AV}$ | P-Wave Detected During An Atrial Refractory Period During An AV/PV Interval |

For periods of time when the pacemaker is operating in the single-chamber mode, the pacemaker stores paced, sensed, $P_{REF}$ and $R_{REF}$ events, rather than all of the events of TABLE II.

Other internal components of pacemaker 10 of FIG. 1 operate to receive programming signals from an external programmer (FIG. 2) and to modify the operation of the pacemaker in accordance with the programming signals. Each time the pacemaker receives programming signals, the pacemaker records a record of the corresponding "programming event" as an event record for subsequent transmission to the external programmer for display thereon in a graphical format. TABLE III provides a list of programming events stored by the pacemaker 10 of FIG. 1.

TABLE III

| PROGRAMMING EVENT NAME | PROGRAMMING EVENT TYPE |
|---|---|
| Mode | Pacemaker Mode Programmed |
| Base Rate | Heart Base Rate Programmed |
| Rest Rate | Heart Rest Rate Programmed |
| Maximum Tracking Rate | Maximum Pacemaker Tracking Rate Programmed |
| Maximum Sensor Rate | Maximum Pacemaker Sensor Rate Programmed |
| Rate Responsive AV/PV Delay | Rate Responsive AV/PV Delay Programmed |

Still other internal components operate to automatically trigger pacemaker operations based upon the condition of the patient as sensed by the pacemaker. Such "patient condition-triggered events" are also stored within event records for subsequent transmission to, and display on, the external programmer. TABLE IV provides a list of all patient condition-triggered events stored using event records by pacemaker 10.

TABLE IV

| PATIENT-CONDITION TRIGGERED EVENT NAME | PATIENT-CONDITION TRIGGERED EVENT TYPE |
|---|---|
| Auto-mode Switching | Pacemaker Mode Automatically Switched |
| PMT Detection | Pacemaker Mediated Tachycardia (PMT) Detected |
| PVC Detection | Premature Ventricular Contraction (PVC) Detected |
| Rate Hysteresis | Rate Hysteresis Search Performed |

Still other internal components operate to automatically trigger pacemaker operations based upon the condition of the pacemaker itself, such as a battery test operation triggered in response to the detection of a low battery voltage. A record of such "pacemaker condition-triggered events" are also stored within event records. TABLE V provides a list of all patient condition-triggered events stored using event records by pacemaker 10.

TABLE V

| PACEMAKER-CONDITION TRIGGERED EVENT NAME | PACEMAKER-CONDITION TRIGGERED EVENT TYPE |
|---|---|
| Battery Test | Battery Voltage Test Performed |
| VARIO Test | Minimum Capture Test Performed |
| Diagnostic Data Suspension | Diagnostic Data Suspended |
| Lead Supervision | Lead Fault Detection Test Performed |
| RRT Test | Recommended Replacement Time (RRT) Battery Test Performed |

Thus TABLES II–V list exemplary events stored by the pacemaker of the presently-described exemplary embodiment of the invention within event records. In other embodiments, not all of the events listed in the TABLES may be recorded. In still other embodiments, additional events may also be recorded. As can be appreciated, a wide range of variations are permissible within the scope of the invention.

As noted, the various event records are stored within the pacemaker for subsequent transmission to, and display using, the programmer (FIG. 2) within a graphical display format. Alternatively, if the external programmer is currently in communication with the pacemaker, the event records may be immediately transmitted to the programmer as they are recorded.

The specific format with which the different types of events are stored and otherwise processed differs somewhat depending upon the type of event. In particular, the sensed events listed in TABLE II may be stored in a different format from the various operational events listed in Tables III–V. The format for storing the operational events of TABLE II–V is referred to herein as an "event control records". As will be described below, event control records are handled somewhat differently during the generation of some of the displays presented by the external programmer.

Figure 2:
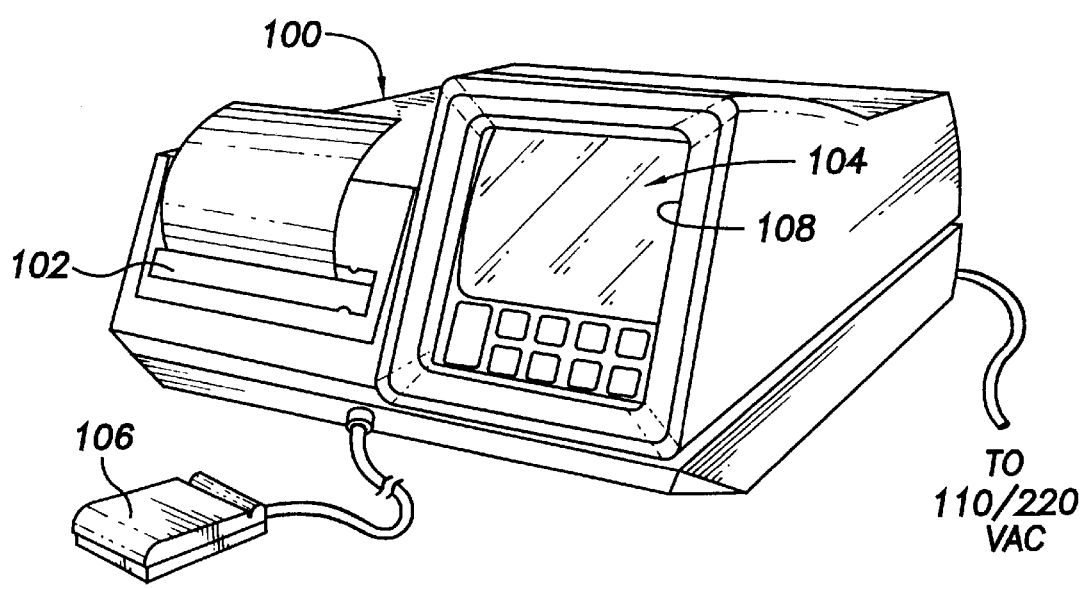
FIG. 2 is a perspective view of an external programmer that may be used for communicating with the implantable pacemaker of FIG. 1.

FIG. 2 illustrates an external programmer 100 configured for receiving the aforementioned event records from pacemaker 10 (FIG. 1) and for generating graphical displays or printouts of the event records. Programmer 100 includes a printer 102 for printing out a graphical representation of the information contained within the event records and a display screen 104 for displaying the graphical representation. Generation of the graphic displays is subject to the control of a physician or other user operating the external programmer. To this end, external programmer 100 presents various menus on display screen 104 for use in controlling operation of the programmer to program pacemaker 10 (FIG. 1) to perform any of the functions listed above in TABLE III. Various menus are also presented on display screen 104 for use in controlling operation of the programmer to generate displays on display screen 104 of information received from the pacemaker including the aforementioned graphical representations of the event records representative of the events listed above in TABLES II–V. Programmer 100 receives menu selections from the physician through a touch screen 108 which overlays display screen 104. Actual programming of the pacemaker is achieved using a telemetry head 106 which, in use, is placed in proximity to the pacemaker.

With reference to FIGS. 3 and 4, internal components of pacemaker 10 and programmer 100 that are pertinent to the processing of event records within the pacemaker and to the generation of event record displays using the external programmer will now be described. Components of programmer 100 are shown in FIG. 3. Components of pacemaker 10 are shown are shown in FIG. 4. Referring first to FIG. 3, a controller 110 of programmer 100 controls graphic display 104 to display the aforementioned menus from which the physician may select, among other options, to program the operation of the pacemaker or to generate graphical displays of the event records previously recorded by the pacemaker.

Assuming first that the physician chooses to program the pacemaker, a program function selection unit 112 controls graphic device 104 to display a list of the programming options corresponding to the programming events listed in TABLE II, i.e. the graphic device displays a list of the following programming options: Mode, Base Rate, Rest Rate, maximum Tracking Rate, Maximum Sensing Rate, and Rate Responsive AV/PV Delay. (Further information regarding these programming options may be found in the above-referenced patents.) The physician selects one or more of the programming options from the list then enters any pertinent parameters, such as the applicable pacemaker mode, rate value or delay value, on one or more display screens (not separately shown) presented by programmed function selection unit 112 using graphical display 104. A command transmitter unit 114 of telemetry head 106 transmits the appropriate command signals to pacemaker 10 to program the pacemaker in the selected manner.

Referring to FIG. 4, the programming signals transmitted by programmer 100 are received by a command receiver unit 116. A controller 118 operates in response to the received commands to program the appropriate pacemaker functional units (not shown) to perform the selected operations in response to the programming signals. Additionally, the programming signals are forwarded by command receiver unit 116 to a programmed function storage unit 120 which stores information pertaining to the received programming command as an event control record (along with the date and time that the command was received) in an event data storage unit 122 to thereby maintain a record of the receipt of the programming signal for subsequent access. Event data storage unit 122 may be a circular buffer configured as described in the Snell et al. patent.

The event data storage unit additionally stores a wide variety of other pacemaker event information including event records corresponding to any of the other events listed within TABLES II–V. To this end, pacemaker 10 additionally includes pacemaker condition-triggered function unit 123, a patient condition-triggered function unit 125 and a sensed event detection unit 127, each of which operates continuously and automatically within the pacemaker (subject to the overall control of controller 118) to detect particular events, trigger responsive operations and record information pertaining to the detected events within event data storage unit 122. The specific information to be recorded along with each event varies depending upon the particular event. For example, for the sensed events of TABLE II, the rate at which the event was detected is stored along with an identification of the type of sensed event and the date and time at which the event was detected. For the events of Tables III–V, the corresponding event control record that is stored includes an identification of the type of event, the date and time at which the event occurred and any additional pertinent information. For example, for an auto-mode switching event, the event control records stored additionally contains an identification of the previous pacemaker mode and the new pacemaker mode. For a battery test event, the event control record additionally stores an indication of whether the battery failed the test.

Now the purpose of the various functional units of the pacemaker of FIG. 4 will be described. Pacemaker condition-triggered function unit 123 continuously monitors the operation of other units of the pacemaker, such as the pacemaker battery (not shown) and triggers appropriate operations in response thereto. More specifically, pacemaker condition-triggered function unit 123 triggers a battery test, a VARIO test, a lead supervision test and an RRT criteria test. The battery test is periodically performed to determine if the battery has sufficient power by, for example, determining if the battery voltage has fallen below a predetermined minimum threshold and, if so, appropriate warning signals are generated. Also, the pacemaker may modify its own operations, perhaps to suspend further diagnostic data acquisition to save battery power. The VARIO test is a minimum capture test performed to determine the minimum voltage of a stimulation pulses sufficient to be captured and responded to by the heart. Typically, the voltage level for stimulation pulses is then set based upon the minimum capture threshold to ensure that a minimum amount of energy is used in each stimulation pulse while still ensuring adequate capture of the pulse. The lead fault detection test (also referred to a Lead Supervision test) is periodically performed to test the integrity of the electrical leads (FIG. 1) perhaps by sensing the impedance thereof. The recommended replacement time (RRT) test is periodically performed to determine if the battery, or other power source of the pacemaker, should be replaced and, if so, appropriate warning signals are generated. The RRT test differs from the previously-described battery test in that a more sophisticated set of tests are performed. Additionally, pacemaker condition-triggered function unit 123 may selectively suspend the further acquisition of diagnostic data. This is typically done if the battery begins to lose power. By suspending diagnostic data acquisition, a greater amount of remaining battery power is thereby preserved for sensing and pacing the heart.

Each time an operation is triggered by pacemaker condition-triggered function unit 123, the unit also operates to store an event control record within data storage unit 122 representative of the triggered event. Accordingly, each of the events listed in TABLE III, above, may be recorded within the data storage unit.

Patient condition-triggered function unit 125 continuously monitors the status of the patient's heart via an electrical sensor unit 129 connected to leads 14 and 16 (FIG. 1) and triggers appropriate operations in response to certain detected conditions. More specifically, patient condition-triggered function unit 125 triggers automode switching, PMT detection, PVC detection and an rate hysteresis operation. Automode switching is performed to automatically switch the pacing mode of the heart to, for example, switch from a dual mode to a single chamber mode. PMT detection is performed continuously to detect a pacemaker mediated tachycardia such as an endless loop tachycardia, a tracking atrial fibrillation. PMT is also referred to as pacemaker reentry tachycardia, circus tachycardia or endless loop tachycardia. If PMT is detected, appropriate responsive therapy is automatically performed by the pacemaker in an attempt to terminate the PMT. For example, atrial sensing may be terminated via an automode switching operation. PVC detection is performed continuously to detect premature ventricular contractions (i.e. ventricular contractions occurring during a pre-defined refractory period). The physician may elect to shorten the refractory period to ensure that PVC pulses are properly sensed. Proper sensing of PVC's may be helpful in eliminating or preventing PMT's. The rate hysteresis search is performed periodically to set the hysteresis escape rate. The hysteresis escape rate is typically set to a value less than the base rate to inhibit pulse generation in some circumstances to allow the heart further time to generate its own pulse.

Each time an operation is triggered by patient condition-triggered function unit 125, the unit also operates to store an event control record within data storage unit 122 representative of the triggered event. Accordingly, each of the events listed in TABLE IV, above, may be recorded within the data storage unit.

Sensed event detection unit 127 continuously monitors the signals received from the patient's heart to detect selected events and records pertinent information pertaining to the events within the data storage unit. More specifically, sensed event detection unit 127 detects each of the events listed in TABLE II. The last three events, namely $P_{REF}, R_{REF}$ and $P_{AV}$, are events occurring during a refractory period following generation of a stimulation pulse. Knowledge of these refractory events is helpful to the physician in setting refractory periods and the like.

Thus while pacemaker 10 of FIG. 1 is in operation, it continuously monitors various aspect of its condition and the condition of the patient in which it is implanted and stores appropriate diagnostic information as event records in event data storage unit 122. Additionally, as noted above, the pacemaker may receive programming commands which are also stored in the data storage unit.

Ultimately, the physician may wish to display diagnostic information pertaining to any of the events previously recorded. Such may be desirable during a follow-up session with the patient in which the pacemaker is implanted. To display the diagnostic information, the physician then selects for the display of recorded events (by using appropriate menus not separately shown herein displayed by graphic device 104 of FIG. 3). Controller 110 forwards appropriate event record retrieval commands to pacemaker 10 (FIG. 4) via command transmitter unit 114 of telemetry head 106. The retrieval commands are received by command receiver unit 116 of the pacemaker of FIG. 4 and forwarded to an event record access unit 131 which retrieves all stored event records from event data storage unit 122 for transmission to the programmer via a data transmitter unit 130. The event records are received by a data receiver unit 132 of telemetry head 106 of the programmer of FIG. 3 and forwarded to an event display generation unit 134. The event display generation unit operates to display a representation of the event records using either graphic device 104, printer 102, or both. Additionally, the event display generation unit may trigger an annunciator 136 to generate an audible sound upon the display of certain event records to help direct the physician's attention to the display.

A variety of graphical displays of information contained within the event records may be generated under control of the physician. In the presently described exemplary embodiment, the following graphical displays of information contained within the event records may be displayed under the control of the physician: event record displays, event bar graphs, rate bar graphs, rate time graphs, and event time graphs. The event record display presents the various detected events of Tables II–V and the corresponding pacing rate with respect to the time of the occurrence of the event. Briefly, for periods of time while the pacemaker is in a dual-chamber mode (such as DDD, DDI etc.), the events presented include PV, PR, AV (or V when the mode is VDDR or VDD), AR and PVC (premature ventricular contraction). For periods of time while the pacemaker is in a single-chamber mode (such as VVI, AAI etc.), the events are presented merely as paced or sensed. The event bar graph presents a histogram of different event types listing the total number of counts of each event type for a presented period of time. The event time graph presents histograms of event types vs. time of event occurrence. The rate bar graph presents histograms of sensed and paced events vs. their rate. The rate time graph presents histograms of rates vs. times. In other embodiments, more or fewer displays may be generated. Details of the manner by which the various event record displays are generated are provided in the Snell et al. patent. Accordingly, the following descriptions will be directed primarily to the portions of selected displays containing additional information not provided by the display screens of the Snell et al. patent.

Figure 5:
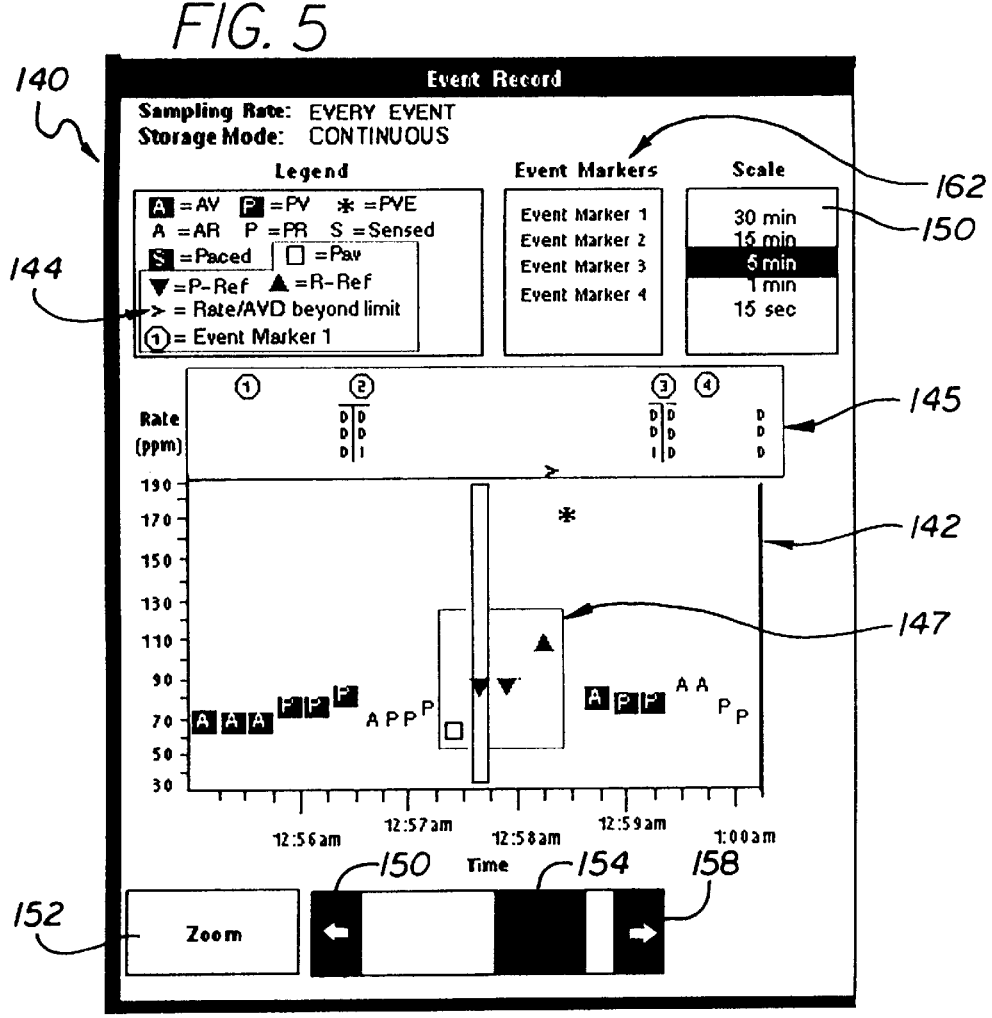
FIG. 5 is an exemplary event record screen displayed by the external programmer device of FIG. 3.

FIG. 5 illustrates an exemplary event record display screen 140 for events recorded during a period of time when the pacemaker was in a dual-chamber mode. The event record display screen includes a graphical display 142 of recorded events shown using various graphical icons distributed along a horizontal time-axis and a vertical rate axis. The events displayed may include any of the events listed in the TABLES above. The sensed events of TABLE II are represented each by a unique icon positioned along the time-axis of the graphic display at the time at which the events as sensed are recorded within the corresponding event record and positioned along the rate axis at a location representative of the rate at which the event was sensed. In the example of FIG. 5, rates are scaled between 30 and 190 pulses per minute (ppm). Legend 144 provides a summary of the unique graphical icons presented in display 142 such as: an A for an AR event; a P for PR event; a square black box with a reverse video 'A' for an AV event; a square black box with a reverse video 'P' for a PV event; a '*' for a PVE event; a white square box for a $P_{AV}$ event; an upside down black triangle for $P_{REF}$ event; a back triangle for $R_{REF}$ event; etc. All other events (i.e. the events listed in Tables III–V) are identified as 'event markers' and are graphically represented by sequential arabic numerals each within a circle, such as a 1 in a circle. The event markers themselves are displayed along a top portion 145 of graphical display 142 at a point along the time-axis corresponding the time at which the event was recorded by the pacemaker. The event markers, however, are not scaled along the vertical rate axis. For an automode switching event, in addition to providing an arabic numeral in a circle, the previous and subsequent pacemaker modes are also displayed (e.g. DDD v. DDI).

For data collected during a period of time when the pacemaker was in a single-chamber mode, the event record display shows a solid black square box with a reverse video 's' for a paced event, an 'a' for a sensed event, an upside down black triangle for a $P_{REF}$ event and a black triangle for an $R_{REF}$ event In the dual-chamber example of FIG. 5, a variety of AV, PV, AR and PR events are shown, along with four refractory period events 147: one $P_{AV}$ event followed by two $P_{REF}$ events and a single $R_{REF}$ event. The latter $R_{REF}$ event is followed by a star icon indicated the first subsequent sensed event.

The event record display also provides a selectable time scale list 150 to allow the physician to select the time scale over which data is to be displayed within graphical display 142. As shown, exemplary time scales include fifteen seconds, one minute, five minutes, fifteen minutes and thirty minutes. Although not shown, additional time scales include one hours, two hours, five hours, twelve hours, thirty hours, sixty hours, one hundred twenty hours, one week, two weeks, four weeks, eight weeks, sixteen weeks, thirty weeks, and fifty-two weeks. Depending upon the time scale, the event record display may not be able to show all individual events. If so, the event record display presents a compressed display with time slots providing the maximum, minimum and average rates of the events within the time slots.

The event record display also provides a ZOOM button 152 which, upon selection, causes the external programmer to selectively display only a portion of the previous event record display. At that time, the ZOOM button is replaced with an UN-ZOOM button to allow for a return to the previous display. Furthermore, the event record display includes a time bar 154 which graphically indicates the portion of the total amount of event record data received from the pacemaker that is currently displayed. In the example of FIG. 5, only about one third of the total event record data retrieved from the pacemaker is displayed. Selection of one of the arrow buttons 156 and 158 causes the graphical display to be scrolled to the left or right, respectively, to display other portions of the event record data received from the pacemaker. Additionally, a vertical line 160 is displayed to provide a marker to assist the physician in scrolling or otherwise examining data. Although not shown, still other buttons may be presented on the display including, for example, a PRINT button or a CANCEL button.

A selectable event marker list 162 displays a list of the displayed event markers by number. Upon selection of one the events listed in the event marker list, programmer 100 (FIG. 3) generates a pop-up display providing pertinent information pertaining to the selected event marker.

Figure 6:
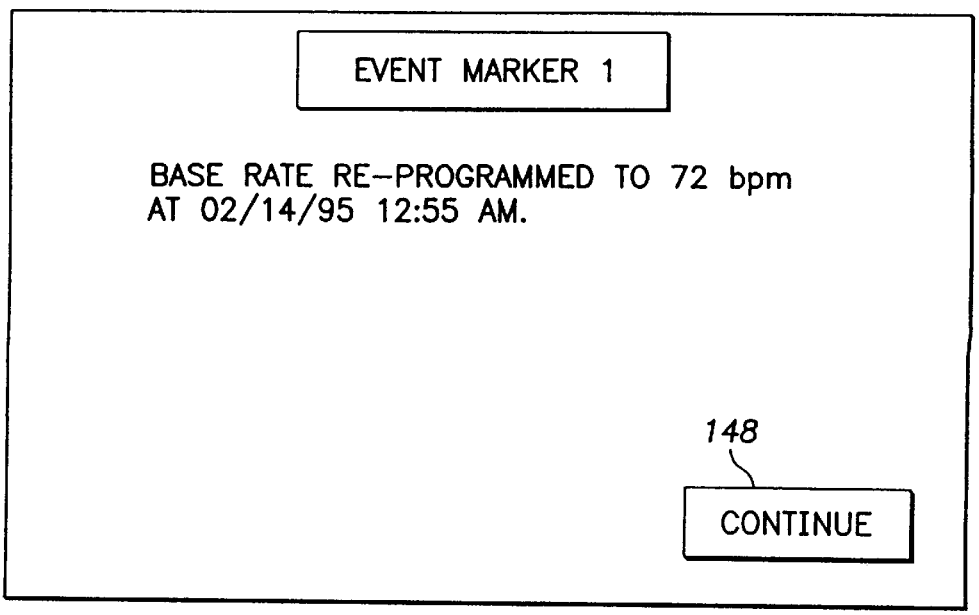
FIG. 6 is an exemplary pop-up display screen displayed by the external programmer device of FIG. 2 providing details of an exemplary programming event that had been recorded by the pacemaker of FIG. 4.

FIG. 6 provides an example of a pop-up display providing information pertaining to one event marker, specifically a "base rate change" programming event recorded by the pacemaker (and identified within FIG. 5 as event marker '1'). As can be seen from FIG. 6, the pop-up display provides a textual description of the base rate programming operation including the new base rate as well as the date and time at which the base rate change occurred. Selection of a CONTINUE button 148 within the pop-op display causes the external programmer to redisplay the event record display of FIG. 5 to allow for selection of another event marker for generation of another pop-up display or for selection of any other appropriate function.

For each different event marker, different information may be provided within the pop-up display. Generally speaking, all pertinent information stored as part of the event control record is displayed. Thus, for example, in the pop-up display generated from a battery test event marker, the pop-up display indicates whether the battery failed the test and additionally displays the date and time. Additional diagnostic information may be presented as well. For example, for a pop-up display generated from an RRT test event marker wherein the recommended replacement has been reached, the following information is presented along with the date and time of the RRT:

"Pulse generator has reached RRT for the following possible reasons:
1. Battery is RRT;
2. Battery is near RRT.
3. RRT Triggered because of high output pacing.
4. RRT was possibly triggered by applied defibrillator/discharge
5. RRT could have been triggered by implantable defibrillator."

Figure 7:
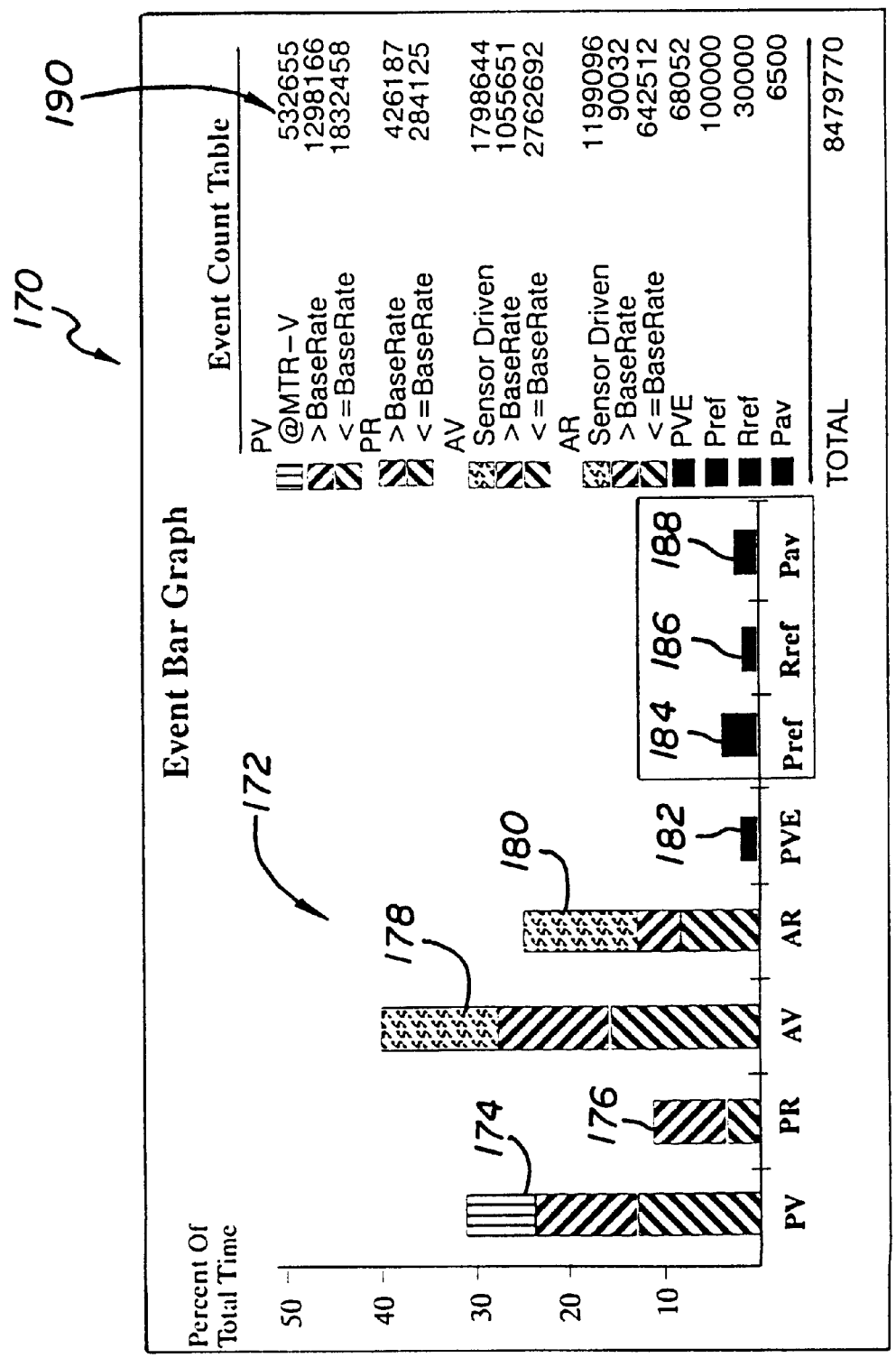
FIG. 7 is an exemplary event bar graph display screen displayed by the external programmer device of FIG. 3.

Referring to FIG. 7, an exemplary event bar graph display 170 is shown having a bar graph 172 providing a set of bars each separately corresponding to one of the sensed events listed in TABLE II, namely PV, PR, AV, AR, PVE and the three refractory period events $P_{REF}$, $R_{REF}$ and $P_{AV}$. The bars are distributed along a vertical axis of the bar graph and extend upwardly along a vertical axis representative of 'Percentage of Total Time'. Each of the bars for the PV, PR, AV, AR events are sub-divided into different sections. More specifically, a PV 174 bar is split into three sections to show the relative percentages of data collected either @MTR-V, above the base rate or below the base rate. A PR bar 176 is split into two sections to show the relative percentages of data collected either above the base rate or below the base rate. An AV bar 178 is split into three sections to show the relative percentages of data either sensor driven, collected above the base rate or collected below the base rate. An AR bar 180 is also split into three sections to show the relative percentages of data either sensor driven, collected above the base rate or collected below the base rate. The remaining bars: a PVE bar 182, a $P_{REF}$ bar 184, a $R_{REF}$ bar 186, and a $P_{AV}$ bar 188 are not individually sub-divided. An event count table 190 is also provided which lists the actual numerical counts of each category of event shown in the event bar graph. For event records recorded during periods of time when the pacemaker was in a single-chamber mode, the event histogram includes only histogram bars for sensed, paced, $P_{REF}$ and $R_{REF}$.

Thus a few exemplary displays of the event record data have been specifically illustrated. Additionally, a variety of other displays are generated by the exemplary embodiment of the invention including the aforementioned event bar graphs, rate bar graphs, rate time graphs, and event time graphs, which each provide different graphical representations of the sensed events of TABLE II. Additionally details regarding the characteristics of those displays are provided in the Snell et al. patent. Of course, it should be understood, that in the exemplary embodiment herein described, each of those displays is modified as appropriate to additionally incorporate the refractory period events $P_{REF}$, $R_{REF}$ and $P_{AV}$. Also, it should be noted that a wide variety of other types of displays of the event records may alternatively be generated in accordance with the principles of the invention. For example, a graphical display may be generated that merely provides a list of all of the event records along with the date and time at which the events were recorded, perhaps arranged in chronological order.

Eventually, the physician terminates the presentation of graphical representations of the event records by selecting an appropriate menu option, such as a CANCEL menu option (not shown), and can thereafter select other programmer operations.

What has been described this far is a first exemplary embodiment of the invention wherein the external programmer generates various printouts or displays of event records based upon information received from the pacemaker. In the following, a second exemplary embodiment of the invention will be described wherein an external programmer generates various printouts or displays of IEGM's and surface ECG's with selected event markers displayed long with the IEGM's and surface ECG'S.

Second Exemplary Embodiment

Referring to FIGS. 8–13, the second exemplary embodiment of the invention will now be described. An external programmer 200 (shown in block diagram form in FIG. 8) receives signals from an implanted pacemaker 201 (shown in block diagram form in FIG. 9) and generates various displays therefrom. Preferably, pacemaker 201 is capable of transmitting all of the same event record information described above in connection with the system of FIGS. 1–7 and external programmer 200 is capable of displaying or printing out all of the same event record displays. Additionally, though, pacemaker 201 also transmits data from which external programmer 200 generates real-time IEGM displays and printouts. Some of the events described above that are displayed using the event record displays, such as automatic mode switching events, are also displayed by external programmer 200 along with the real-time IEGM's. The events are displayed using marker icons positioned adjacent to the IEGM displays. Furthermore, pacemaker 201 transmits some additional types of event information beyond those which are described above, such as atrial or ventricular events detected during a non-absolute refractory period, which are also displayed by the external programmer using event marker icons positioned along with IEGM's. Also, external programmer 200 receives signals from a surface ECG monitoring unit 203 (shown in FIG. 8) from which the external programmer additionally generates displays or printouts of real-time surface ECG's along with the IEGM's and the event markers. As before, the pacemaker can operate in either a dual-chamber mode or a single-chamber mode and the information transmitted by the pacemaker and the displays and printouts generated by the external programmer may differ depending upon the mode.

The components of the system of FIGS. 8–13 are similar to the components of the system of FIGS. 1–7 and only pertinent differences will be described in detail. In particular, the following descriptions will be directed primarily to those components that generate the real-time IEGM/ECG displays and to those components that process event data for displaying event markers along with the real-time IEGM/ECG displays.

TABLES VI–IX set forth the various events that are processed as event marker data and displayed using marker icons in connection with the real-time IEGM/ECG displays.

TABLE VI is a list of sensed events displayed by the external programmer along with IEGM/ECG's for data collected while the pacemaker is operating is the dual-chamber mode. Notably, the events listed in TABLE VI include two events P' and R' detected during non-absolute refractory periods. P' symbolizes atrial activity detected during a non-absolute refractory period and R' symbolizes ventricular activity detected during a non-absolute refractory period.

TABLE VI

| SENSED EVENT NAME | SENSED EVENT TYPE |
|---|---|
| A | Atrial Stimulus |
| V | Ventricular Stimulus |
| P | Atrial Activity Outside Atrial Refractory/Blanking Period |
| R | Ventricular Activity Outside Ventricular Refractory/Blanking Period |
| Length of A Ref. | End of Atrial Refractory Period |
| Length of V Ref. | End of Ventricular Refractory Period |
| P' | Atrial Activity During Non-Absolute Refractory Period |
| R' | Ventricular Activity During Non-Absolute Ventricular Period |

For periods of time when the pacemaker is operating in the single-chamber mode, the pacemaker may store fewer types of event information such as, for example, only A, P, Length of A Ref. and P', rather than all of the events of TABLE VI.

TABLE VII is a list of "programming events" displayed by the external programmer along with IEGM/ECG's.

TABLE VII

| PROGRAMMING EVENT NAME | PROGRAMMING EVENT TYPE |
|---|---|
| EP Test | Electro-Physiological Test (i.e. Physician-Controlled Arrhythmia Event) |

TABLE VIII is a list of "patient condition-triggered" events displayed by the external programmer along with the IEGM/ECG's.

TABLE VIII

| PATIENT-CONDITION TRIGGERED EVENT NAME | PATIENT-CONDITION TRIGGERED EVENT TYPE |
|---|---|
| Auto-mode Switching | Pacemaker Mode Automatically Switched |
| PMT Detection | Pacemaker Mediated Tachycardia (PMT) Detected |
| PVC Detection | Premature Ventricular Contraction (PVC) Detected |
| Rate Hysteresis | Rate Hysteresis Search Performed |
| AV/PV Hysteresis | AV/PV Hysteresis Search Performed |

TABLE IX is a list of "patient condition-triggered events" displayed by the external programmer along with the IEGM/ECG's.

TABLE IX

| PACEMAKER-CONDITION TRIGGERED EVENT NAME | PACEMAKER-CONDITION TRIGGERED EVENT TYPE |
|---|---|
| Battery Test | Battery Voltage Test Performed |

TABLE IX-continued

| PACEMAKER-CONDITION TRIGGERED EVENT NAME | PACEMAKER-CONDITION TRIGGERED EVENT TYPE |
|---|---|
| VARIO Test | Minimum Capture Test Performed |
| Lead Supervision | Lead Fault Detection Test Performed |

Thus TABLES VI–IX list exemplary events displayed by the external programmer along with IEGM/ECG's. In other embodiments, not all of the events listed in TABLES VI–IX are necessarily displayed. In still other embodiments, additional events may also be displayed including, for example, some of the additional events listed above in TABLES II–V. As can be appreciated, a wide range of variations are permissible within the scope of the invention.

Figure 8:
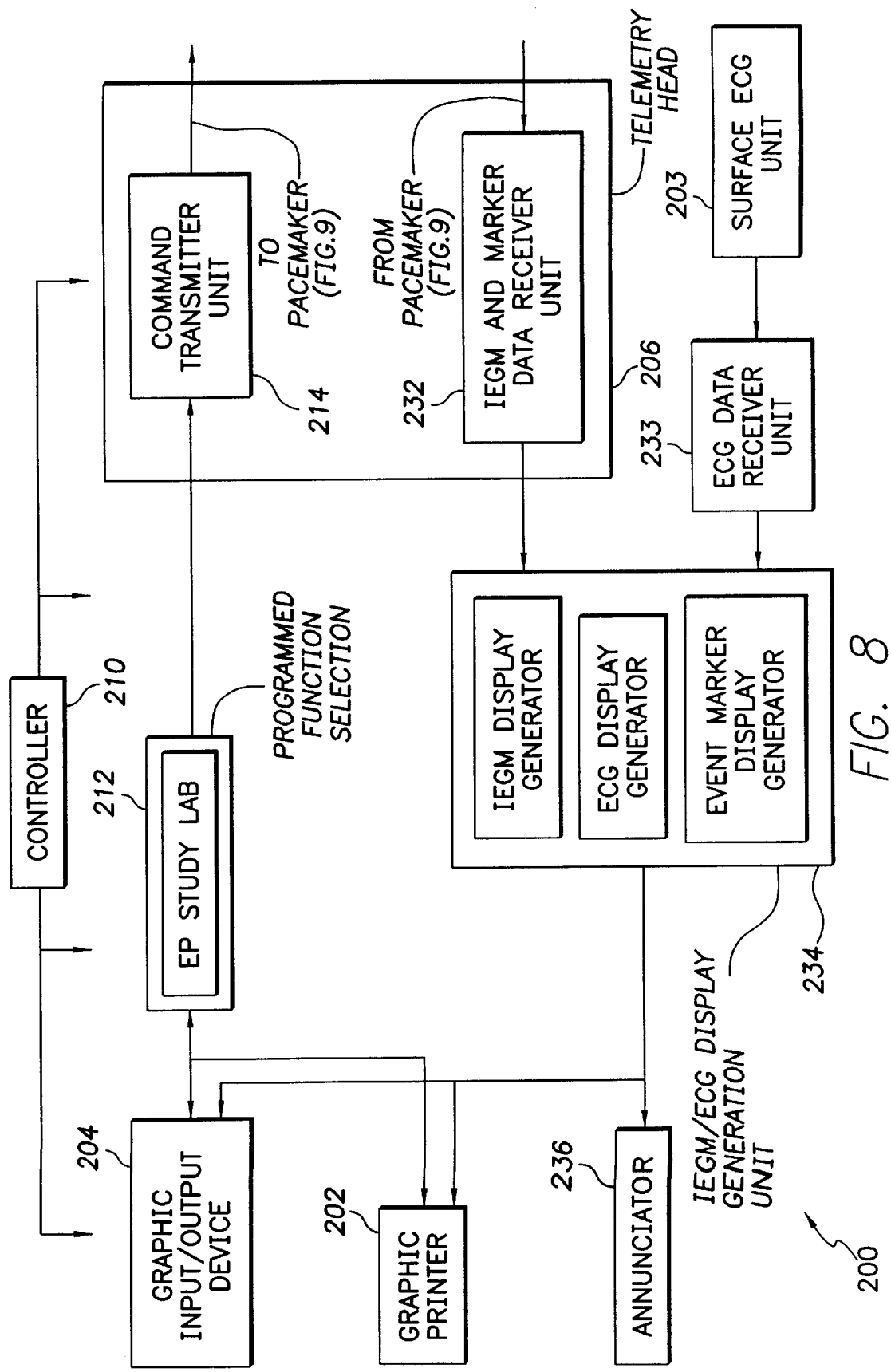
FIG. 8 is block diagram of pertinent components of a second embodiment of the external programmer of FIG. 2 for use in generating and displaying enhanced event markers in connection with IEGM/ECG displays.
Figure 9:
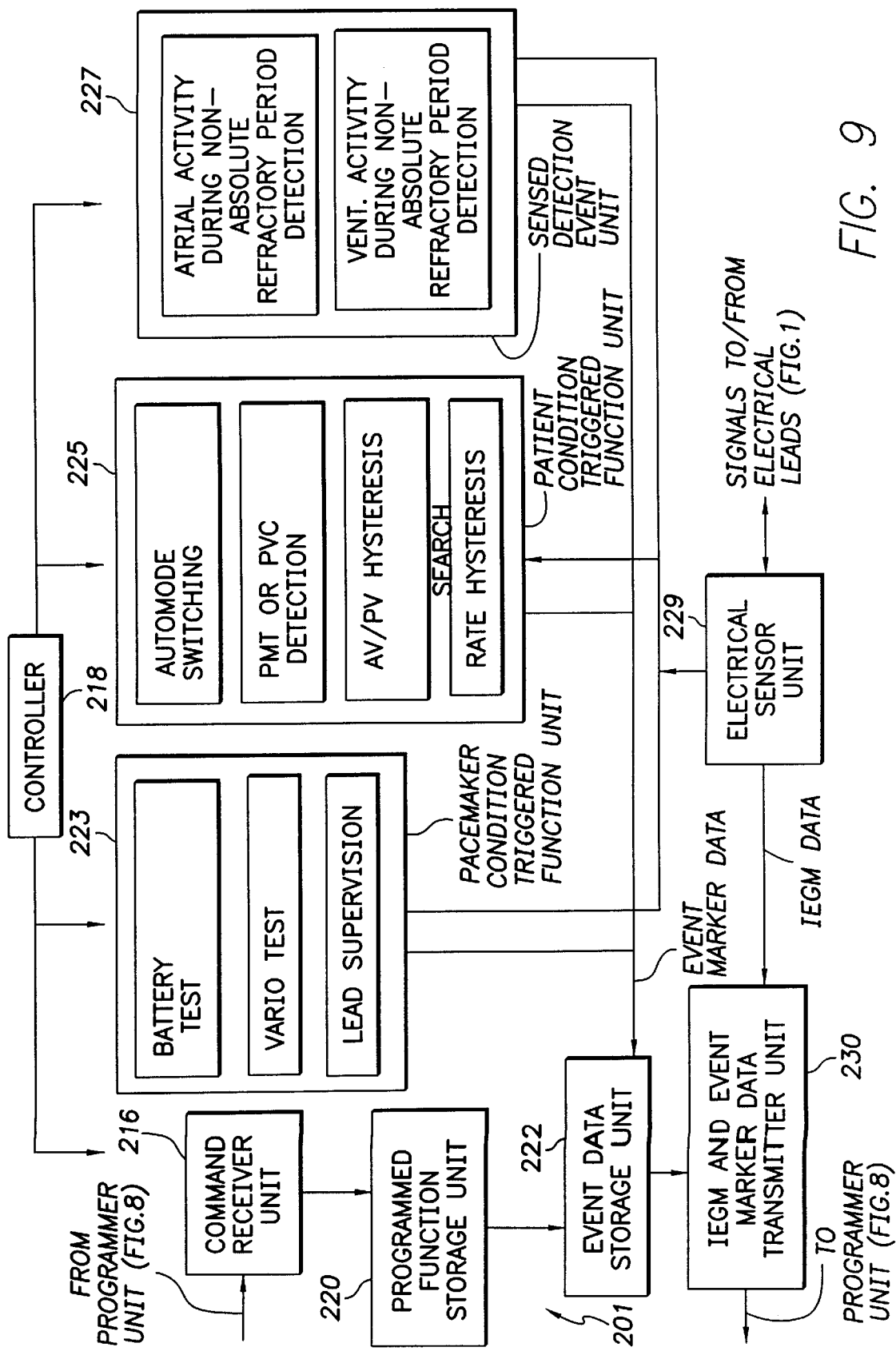
FIG. 9 is block diagram of pertinent components of a second embodiment of the implantable pacemaker of FIG. 1 for use in generating the IEGM displays using the external programmer of FIG. 8.

Referring now to FIG. 8, programmer 200 includes a printer 202 and a display screen 204. External programmer 200 presents various menus on display screen 204 for use in controlling operation of the programmer to program pacemaker 201 (FIG. 9). Various menus are also presented on display screen 204 for use in controlling operation of the programmer to generate displays of information received from the pacemaker including the aforementioned real-time IEGM/ECG displays containing event markers representative of the events listed above in TABLES VI–IX. A controller 210 controls graphic display 204 to display the aforementioned menus. Programmer 200 receives menu selections from a physician through a touch screen 208 which overlays display screen 204. Actual programming of the pacemaker is achieved using a telemetry head 206 which, in use, is placed in proximity to the pacemaker.

As far as the generation of real-time IEGM/ECG displays is concerned, the physician selects for display of IEGM/ECG data via one of the menus presented by display screen 204 under the control of controller 210. Appropriate signals are sent under the control of controller 210 to command transmitter unit 214 of telemetry head 206 for transmission to a command receiver unit 216 (FIG. 9) of the pacemaker 201. A controller 218 of the pacemaker operates to control an electrical sensor unit 229 to begin detecting signals representative of IEGM's using electrical leads (shown in FIG. 1) implanted in the heart. The IEGM signals are forwarded to an IEGM and event marker data transmitter unit 230 for transmission to the external programmer.

An IEGM and marker data receiver unit 232 (FIG. 8) of the telemetry head 206 of external programmer 200 receives the IEGM data and forwards the data to an IEGM/Marker display generation unit 234. IEGM/Marker display generation unit 234 processes the data to generate real-time IEGM displays for presenting on either graphic display device 204, printer 202, or both. If so configured, external programmer 200 also receives ECG data from surface ECG monitoring unit 203 via an ECG data receiver unit 233. The ECG data is also forwarded to IEGM/Marker display generation unit 234 which simultaneously generates ECG displays along with the IEGM displays.

The IEGM/ECG displays are presented in real-time with the data scrolling left to right across the display screen. An exemplary scrolling IEGM/ECG display generated by IEGM/Marker display generation unit 234 is provided in FIG. 10. The IEGM and ECG portions of the display are identified, respectively, by reference numerals 250 and 252. At any time, the scrolling IEGM/ECG display may be frozen, but pressing a button labeled "Freeze" 254, to allow the user to more closely scrutinize potions of the displayed data. Thereafter, the display may be switched back to a continuously scrolling real-time display. An exemplary frozen IEGM/ECG display is provided in FIG. 11. The IEGM and ECG portions of the display are identified, respectively, by reference numerals 256 and 258.

While IEGM/ECG displays are being presented, pacemaker 201 (FIG. 9) may detect any of the various events listed in TABLES VI–IX. If so, event records representative of the detected events are created within the pacemaker and stored within an event data storage unit 222 and also forwarded in real-time to IEGM and event marker data transmitter unit 230 for transmitting, along with the aforementioned IEGM signals, to the external programmer. The event marker data is received along with the IEGM data by IEGM and marker data receiver unit 232 (FIG. 8) of external programmer 200 and forwarded to IEGM/marker display generation unit 234. IEGM/Marker display generation unit 234 processes the marker data to generate icons for displaying along with the IEGM/ECG displays.

Figure 10:
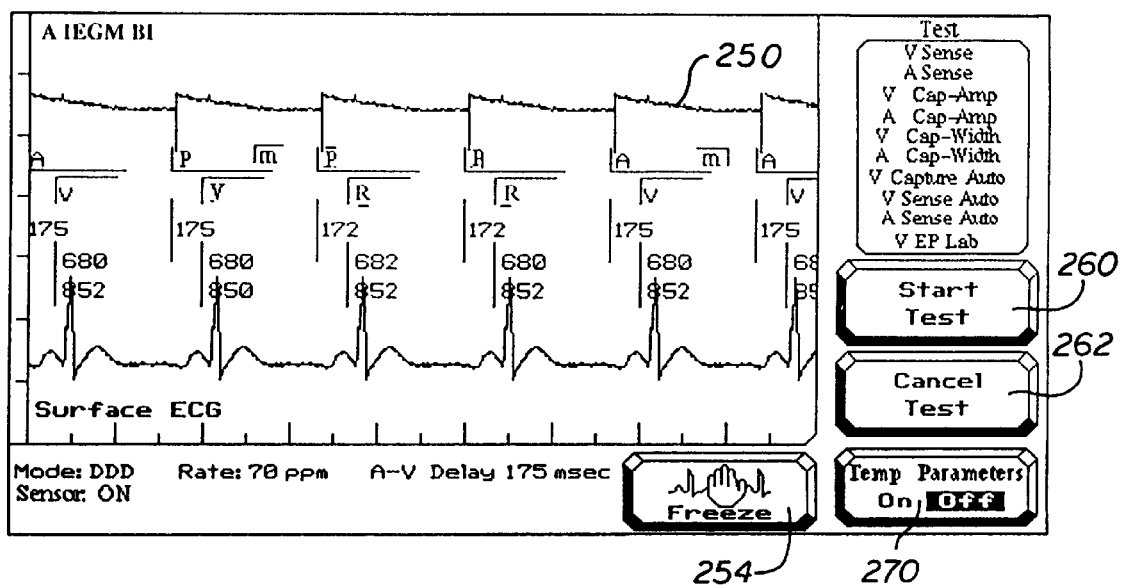
FIG. 10 is an exemplary real-time IEGM display screen presented by the external programmer device of FIG. 8.
Figure 11:
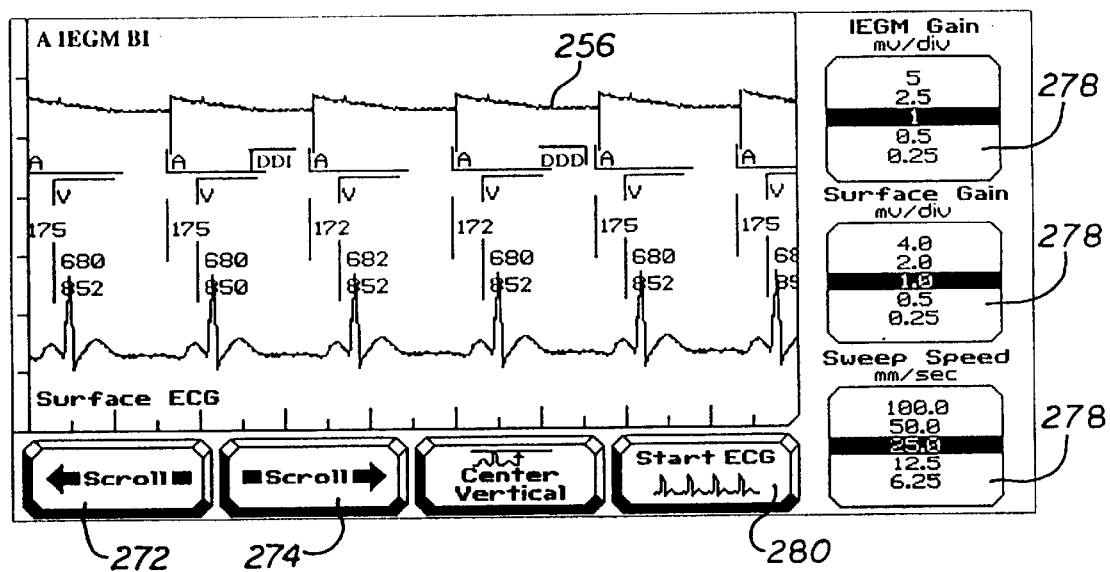
FIG. 11 is an exemplary frozen IEGM display screen presented by the external programmer device of FIG. 8.

Exemplary markers illustrative of sensed events are shown in the examples of FIGS. 10 and 11. More specifically, the scrolling real-time display of FIG. 10 illustrates two automode switching events (both represented by an `m') along with various sensed atrial and ventricular stimulus events (represented by A and V, respectively), and various atrial and ventricular events sensed during non-absolute refractory periods (represented by P' and R'). As to the automode switching events, when the mode is switched, an `m' with a right-facing bracket is displayed adjacent to the IEGM display and a textual notification is provided on the bottom of the display identifying the new mode (e.g. `Mode Switched to DDI'). When the mode switches back, an `m' with a left-facing bracket is displayed and a textual notification is provided on the bottom of the display identifying the mode to which the pacemaker has returned.

As to the choice of particular icons for representing the various other events of TABLES VI–IX, in the presently described example the following icons are used to represent the sensed events of TABLE VI: `A' for atrial stimulus; `V' for ventricular stimulus; `P' for atrial activity outside atrial refractory/blanking period; `R' for ventricular activity outside ventricular refractory/blanking period; `P"' for atrial activity during non-absolute refractory period; `R"' for ventricular activity during non-absolute ventricular period. (In other embodiments, P' is instead represented using a P with an overbar and R' is represented using an R with an underbar.) Horizontal bars of appropriate length are provided to illustrate the lengths of the atrial and ventricular refractory periods. The following icons are used to represent the other events of TABLES VII–IX: `B' for battery test; `V' for VARIO test; the aforementioned `m' for automode switching; and `X' for all of the other events.

The presentation of markers within the frozen display of FIG. 11 are similar to that of the scrolling display of FIG. 10 but, instead of displaying an `m' with a left- or right-facing bracket, the specific modes associated with automode switching events (such as VVI or DDI) are displayed with the appropriate left or right-facing bracket such that the user need not look to the textual display at the bottom of the screen to see that associated modes. Also, rather than use an `X' to represent a variety of different events as in the real-time display, when the system is presenting a freeze mode display, `RHS' is used for rate hysteresis; `A/P VHS' for AV/PV hysteresis search; `PMT' for PMT detection; `PVC' for PVC detection; `EP' for EP test; and `Lead Supv.' for a lead fault detection test.

Although FIGS. 10 and 11 illustrates only a few selected events, in the presently described exemplary embodiment, any of the events listed in TABLES VI–IX are to be displayed within the IEGM/ECG display. In other embodiments, additional events may also be displayed including any of those listed in TABLES II–V.

The manner by which the system processes the various events of TABLES VI–IX for display will now be briefly described with continued reference to FIGS. 8 and 9. As far as the programming events of TABLE VII are concerned, a program function selection unit 212 controls graphic device 204 to display a list of the available programming options, including the induced arrhythmia (EP Test) operation listed in TABLE VII, and the physician selects one or more of the programming options from the list. (As will be described below, the programming options are presented on the right hand side of the real-time IEGM/ECG display (FIG. 10). Alternatively, the programming options are presented using other menu display screens.) Command transmitter unit 214 of telemetry head 206 transmits the appropriate command signals to pacemaker 202 to program the pacemaker in the selected manner. The AV/PV Hysteresis Search is performed to set the AV/PV delay value. The EP Test is performed to temporarily induce arrhythmia. Details regarding EP Tests may be found in U.S. Pat. No. 5,653,737 to van Lake entitled `Programmable pacemaker for noninvasive EP testing for atrial tachycardias with ventricular support' which is incorporated by reference herein.

Referring to FIG. 9, the programming signals transmitted by programmer 200 are received by a command receiver unit 216. Controller 218 operates in response to the received commands to program the appropriate pacemaker functional units (not separately shown) to perform the selected operations in response to the programming signals. Additionally, the programming signals are forwarded by command receiver unit 216 to a programmed function storage unit 220 which stores information pertaining to the received programming command as an event control record in event data storage unit 222. The event record for that programming event is also forwarded in real-time via IEGM and event marker data transmitter unit 230 for transmission to external programmer 200 (FIG. 8) for display thereon using appropriate icons within the real-time IEGM/ECG display.

As to the non-programming events of TABLES VI and VIII–IX, pacemaker 202 employs a pacemaker condition-triggered function unit 223, a patient condition-triggered function unit 225 and a sensed event detection unit 227, each of which operates continuously and automatically within the pacemaker (subject to the overall control of controller 218) to detect particular events, trigger responsive operations and record information pertaining to the detected events within event data storage unit 222. The specific information to be recorded along with each event varies depending upon the particular event.

Pacemaker condition-triggered function unit 223 continuously monitors the operation of other units of the pacemaker, such as the pacemaker battery (not shown) and triggers appropriate operations in response thereto. For example, pacemaker condition-triggered function unit 223 triggers a battery test, a VARIO test and a lead supervision test (described above in connection with FIG. 4.) Each time an operation is triggered by pacemaker condition-triggered function unit 223, the unit also operates to store an event control record within data storage unit 222 representative of the triggered event and the event record for that event is also forwarded in real-time via IEGM and event marker to data transmitter unit 230 for transmission to external programmer 200 for display thereon using appropriate icons within the real-time IEGM/ECG display.

Patient condition-triggered function unit 225 continuously monitors the status of the patient's heart via electrical sensor unit 229 and triggers appropriate operations in response to certain detected conditions. In particular, patient condition-triggered function unit 225 triggers automode switching, PMT detection, PVC detection, a rate hysteresis search operation and an AV/PV hysteresis search operation. As with the aforementioned pacemaker condition-triggered events, each time an operation is triggered by patient condition-triggered function unit 223, the event record for that event is forwarded in real-time to the external programmer for display thereon using appropriate icons within the IEGM/ECG display.

Sensed event detection unit 227 continuously monitors the signals received from the patient's heart to detect selected events and records pertinent information pertaining to the events within the data storage unit. More specifically, sensed event detection unit 227 detects each of the events listed in TABLE VI. The last two events, namely P' and R', are events occurring during a non-absolute refractory period. Knowledge of these events is helpful to the physician in setting refractory periods and the like.

Thus a variety of events are detected by pacemaker 201 of FIG. 9 and forwarded in real-time for display by programmer 200 of FIG. 8 along with IEGM and surface ECG displays. Referring again to the exemplary displays of FIGS. 10 and 11, other information presented in the displays in additional to the aforementioned IEGM/ECG and event markers displays will now be described. Both the scrolling real-time display of FIG. 10 and the frozen display of FIG. 11 provide labels adjacent to the IEGM and ECG waveforms identifying the particular waveform (e.g. `Surface ECG' and `Atrial IEGM BI') and provide labels at the bottom of the display identifying the current pacing mode (e.g. `DDD'), the current heart rate (e.g. 70 ppm), and the current A-V delay value (e.g. 175 msec). Both displays also provided calculated A-V delays and A and V timing intervals along with each displayed complex. For example, for the fourth complex shown in FIG. 10, a calculated A-V delay of 172 msecs is shown along with calculated A and V timing intervals of 680 and 852 msecs.

The scrolling display of FIG. 10 also provides a test window 258 for allowing the user to select any of a variety of tests including the aforementioned EP test. Other selectable tests include V sense, A sense, V Capture-Amp, A Capture-Amp, V Capture-Width, A Capture-Width, V Capture Auto, A Capture Auto, V Sense Auto and A Sense Auto. These later tests are not particularly pertinent to the present invention and will not be described in detail. The selected test is triggered by pressing a `Start Test' button 260 and terminated by pressing a `Stop Test' button 262. As noted, activation of the EP Lab Test is detected by the pacemaker (FIG. 9) and ultimately causes a corresponding marker to be displayed along with the IEGM and ECG displays. Alternatively, the programmer (FIG. 8) itself may simply insert the EP Test marker into the IEGM/ECG display once the test has been activated. However, by having the pacemaker sense the EP Test and send an event record back to the programmer indicative thereof, feedback is thereby provided confirming that the pacemaker did indeed initiate the EP Test.

Figure 12:
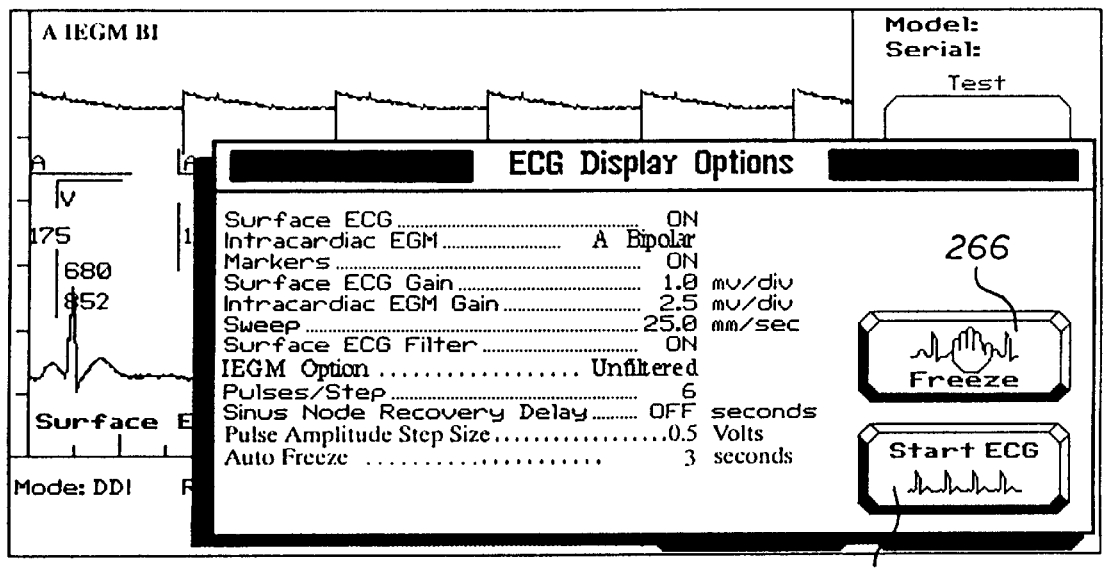
FIG. 12 is an exemplary parameter selection display screen presented by the external programmer device of FIG. 8.

Further with regard to the scrolling display of FIG. 10, at any time the user may press a 'Display Options' button (not separately shown) to present the display of FIG. 12 wherein the user can set or modify a variety of parameters. More specifically, the user may select any of the following:

| Surface ECG | [ON / OFF] |
|---|---|
| IEGM | [OFF / A IEGM UNI / A IEGM BI / A IEGM SPE / V IEGM UNI / V IEGM BI / V IEGM SPE] |
| Markers | [ON / OFF] |
| Surface ECG Gain mv/div | [8.0 / 4.0 / 2.0 / 1.0 / 0.5] |
| IEGM Gain mv/div | [40 / 20 / 10 / 5 / 2.5 / 1 / 0.5] |
| Sweep | [25.0 / 12.5 ] mm/sec |
| Surface ECG Filter | [ON / OFF] |
| IEGM Option | [Filtered / Unfiltered] |
| Pulses/Step | [4 / 5 / 6 / 7 / 8 / 9 / 10] |
| Sinus Node Recovery Delay | [OFF / 2 / 3 / 4 /5] Seconds |
| Auto Freeze | [OFF / 1 / 2 / 3 / 4 / 5] Seconds |
| Pulse Amplitude Step Size | [.25 / .5] Volts |

Within the display of FIG. 12, the currently selected parameter is displayed in bold. The Sinus Mode Recovery Delay can only be set in conjunction with the EP Test. The Auto Freeze mode is only set in conjunction with a Auto Sense Test. The Surface ECG filter and IEGM Option parameters control the operation of ECG and IEGM filters within the programmer (not separately shown in the figures) which filter the IEGM and ECG data to provide a cleaner display of the data. Also, within the options display of FIG. 12, the user may trigger a freeze mode using button 266 or a start or stop ECG displays using button 268.

Also with regard to the scrolling display of FIG. 10, at any time the user may press a 'Temp Parameters' button 270 to activate the usage of alternative temporary programmer parameters rather than the primary programmed parameters. More specifically, the user may temporarily re-set: the pacing mode (e.g. DDDR instead of VVIR) the rate (e.g. 70 instead of 60 ppm); the sensor state (e.g. passive instead of active); the A-V delay value (e.g. 150 instead of 125); the ventricular pulse configuration (e.g. bipolar instead of unipolar); the ventricular sense configuration (e.g. bipolar instead of unipolar tip), the atrial pulse configuration (e.g. bipolar instead of unipolar) and the atrial sense configuration (e.g. bipolar instead of unipolar tip). Upon selection of the Temp Parameters button, an appropriate display (not shown in the figures) is presented to the user to allow for selection of any of the aforementioned temporary alternative parameters.

As to the freeze display of FIG. 11, alternative control buttons are provided instead of those of the continuously scrolling display of FIG. 10. In particular, left and right scroll bars 272 and 274 are provided to allow the user to selectively and slowly scroll the display to the left or right to see additional graphical information not currently displayed. Also a Center Vertical button 276 allows the display to be vertically centered. Additionally, the user may select IEGM gain, Surface Gain and Sweep Speed via input windows 278. Finally, a 'Start ECG' button 280 allows for the surface ECG display to be selectively activated and de-activated.

At any time while the frozen or continuously scrolling IEGM/ECG displays are presented, the user may select for a printout of a portion of the displayed data by pressing an appropriate display button (not shown). FIG. 13 provides an exemplary printout. As can be seen, the printout provides IEGM/ECG displays with appropriate markers and additionally provides a variety of other information including patient information, a list of pertinent ECG/IEGM parameters and a list of the primary vs. temporarily programmed parameters.

Eventually, the physician terminates the presentation of the IEGM/ECG displays by selecting an appropriate menu option and can thereafter select other programmer operations such as the generation of event record displays as described above in connection with FIGS. 1–7.

What has been described are systems for generating, storing, processing and graphically displaying a wide variety of information pertaining to events detected by a pacemaker. The various functional components of the exemplary system may be implemented using any appropriate technology including, for example, microprocessors running software programs or application specific integrated circuits (ASIC'S) executing hard-wired logic operations. Although described with respect to a pacemaker used in conjunction with an external programmer, aspects of the invention are applicable to other systems, such as systems employing other implantable medical devices or systems employing other types of external interfaces for use with the implantable device. The exemplary embodiments of the invention described herein are merely illustrative of the invention and should not be construed as limiting the scope of the invention.

What is claimed is:

1. A method for detecting and displaying information using a remote programming device, an implantable medical device in electrical communication with selected heart tissue, and an external display device, wherein the remote programming device includes a transmitter for transmitting signals to the implantable medical device, wherein the implantable medical device includes a receiver for receiving signals from the remote programming device, functional units for performing operations in response to the received signals, a storage unit for storing signals representative of the operations performed, a sensor for sensing intracardiac electrogram signals within heart tissue connected to the implantable medical device and a transmitter for transmitting signals to the external display device, and wherein the external display device includes a receiver for receiving signals from the implantable medical device and a display for displaying intracardiac electrograms and for generating and displaying icons, said method comprising the steps of:

detecting intracardiac electrogram signals using the sensor of the implantable medical device;

transmitting programming signals from the transmitter of the remote programming device to the receiver of the implantable medical device;

performing operations using the functional units of the implantable medical device in response to the received programming signals;

storing signals representative of the operations in the storage unit;

transmitting, from the transmitter of the implantable medical device to the receiver of the external display device, the intracardiac electrogram signals along with the signals representative of the operations performed within the implantable medical device in response to the programming signals; and in response to the signals received by the external display device, generating icons using the display wherein the icons are representative of the operations performed by the implantable medical device in response to the programming signals and graphically displaying the intracardiac electrogram signals along with the icons.

2. The method of claim 1, wherein the external display device further includes a surface electrocardiogram signal receiver unit and wherein the method further includes the steps of:

receiving surface electrocardiogram signals using the surface electrocardiogram signal receiver unit of the external display device; and graphically displaying the surface electrocardiogram signals using the display device along with the intracardiac electrogram signals and the icons representative of the programming operations performed in response to the programming signals.

3. The method of claim 1, wherein the step of transmitting programming signals from the transmitter of the remote programming device to the receiver of the implantable medical device includes the step of transmitting a signal indicating that arrhythmia is to be artificially induced by the implantable medical device.

4. The method of claim 1, wherein the external display device is part of the remote programming unit.

5. A system for detecting and displaying information received from an implantable medical device connected to heart tissue, said system comprising:

means for receiving intracardiac electrogram signals from the implantable medical device;

means for receiving signals from the implantable medical device representative of programming operations performed within the implantable medical device in response to programming signals received by the implantable medical device;

means for generating icons representative of programming operations performed within the implantable medical device; and means for graphically displaying intracardiac electrogram signals received from the implantable medical device along with icons representative of programming operations performed within the implantable medical device.

6. The system of claim 5, further comprising means for receiving surface electrocardiogram signals and wherein said means for graphically displaying intracardiac electrogram signals and icons additionally displays surface electrocardiogram signals.

7. The system of claim 5 wherein the means for receiving signals from the implantable medical device receives a signal representative of artificially induce arrhythmia.

8. The system of claim 5, wherein said means for receiving intracardiac electrogram signals, said means for receiving signals from the implantable medical device representative of programming operations, said means for generating icons; and said means for graphically displaying intracardiac electrogram signals along with icons each operate in real-time.

9. A method for detecting and displaying information using an implantable medical device and an external display device, wherein the implantable medical device includes functional units for sensing conditions, performing operations in response to the sensed conditions, and for generating signals representative of the operations, an intracardiac electrogram sensor for sensing intracardiac electrogram signals within heart tissue connected to the implantable medical device and a transmitter for transmitting signals to the external display device, and wherein the external display device includes a receiver for receiving signals from the implantable medical device and a display for displaying intracardiac electrograms and for generating and displaying icons, said method comprising the steps of:

sensing conditions using the functional units of the implantable medical device;

performing operations using the functional units of the implantable medical device in response to the sensed conditions;

detecting intracardiac electrogram signals using the intracardiac electrogram sensor of the implantable medical device;

transmitting, from the transmitter of the implantable medical device to the receiver of the external display device, the intracardiac electrogram signals along with the signals representative of the operations performed within the implantable medical device in response to the sensed conditions; and in response to the signals received by the external display device, generating icons using the display wherein the icons are representative of the operations performed by the implantable medical device in response to the sensed conditions and graphically displaying the intracardiac electrogram signals along with the icons.

10. The method of claim 9, wherein the external display device further includes a surface electrocardiogram signal receiver unit and wherein the method further includes the steps of:

receiving surface electrocardiogram signals using the surface electrocardiogram signal receiver unit of the external display device; and graphically displaying the surface electrocardiogram signals using the display device along with the intracardiac electrogram signals and the icons representative of the operations performed in response to the sensed conditions.

11. The method of claim 9, wherein the step of sensing conditions using the implantable medical device includes the step of sensing conditions within a patient in which the medical device is implanted.

12. The method of claim 11, wherein the functional units of the implantable medical device include an auto-mode switching unit and wherein the step of performing operations includes the step of performing auto-mode switching.

13. The method of claim 11, wherein the functional units of the implantable medical device include a pacemaker rate hysteresis unit and wherein the step of performing operations includes the step of performing a pacemaker rate hysteresis search.

14. The method of claim 11, wherein the functional units of the implantable medical device include an AV/PV hysteresis unit and wherein the step of performing operations includes the step of performing an AV/PV hysteresis search.

15. The method of claim 11, wherein the functional units of the implantable medical device include a pacemaker mediated tachycardia (PMT) detection unit and wherein the step of sensing conditions includes the step of detecting PMT.

16. The method of claim 11, wherein the functional units of the implantable medical device include a premature ventricular contraction (PVC) detection unit and wherein the step of sensing conditions includes the step of detecting PVC.

17. The method of claim 11, wherein the step of sensing conditions using the implantable medical device includes the step of sensing parameters representative of the performance of the implantable medical device.

18. The method of claim 17, wherein the functional units of the implantable medical device include a battery test unit and wherein the step of performing operations includes the step of performing a battery test.

19. The method of claim 17, wherein the functional units of the implantable medical device include a minimum capture test unit and wherein the step of performing operations includes the step of performing a minimum capture test.

20. The method of claim 17, wherein the functional units of the implantable medical device include a lead fault detection unit and wherein the step of performing operations includes the step of performing a lead fault detection test.

21. A system for detecting and displaying information received from an implantable medical device, said system comprising:

means for receiving intracardiac electrogram signals from the implantable medical device;

means for receiving signals from the implantable medical device representative of operations performed by the implantable medical device in response to conditions sensed by the implantable medical device;

means for generating icons representative of operations performed within the implantable medical device; and means for graphically displaying intracardiac electrogram signals along with icons representative of operations performed within the implantable medical device.

22. The system of claim 21, further comprising means for receiving surface electrocardiogram signals and wherein the means for graphically displaying intracardiac electrogram signals and icons also displays surface electrocardiogram signals.

23. The system of claim 21, wherein the means for receiving signals from the implantable medical device receives signals representative of operations performed by the implantable medical device based upon the conditions sensed within the patient.

24. The system of claim 23, wherein the means for receiving signals from the implantable medical device receives signals representative the detection of pacemaker auto-mode switching.

25. The system of claim 23, wherein the means for receiving signals from the implantable medical device receives signals representative the detection of pacemaker mediated tachycardia (PMT).

26. The system of claim 23, wherein the means for receiving signals from the implantable medical device receives signals representative the detection of premature ventricular contraction (PVC).

27. The system of claim 23, wherein the means for receiving signals from the implantable medical device receives signals representative the performance of a pacemaker rate hysteresis search.

28. The system of claim 23, wherein the means for receiving signals from the implantable medical device receives signals representative the performance of an AV/PV rate hysteresis search.

29. The system of claim 21, wherein the means for receiving signals from the implantable medical device receives signals representative of operations performed by the implantable medical device based upon the performance parameters sensed within the implantable medical device.

30. The system of claim 29, wherein the means for receiving signals from the implantable medical device receives signals representative the performance of a battery test.

31. The system of claim 29, wherein the means for receiving signals from the implantable medical device receives signals representative the performance of a minimum capture test.

32. The system of claim 29, wherein the means for receiving signals from the implantable medical device receives signals representative the performance of a lead fault detection test.

33. A system for detecting and displaying information received from an implantable medical device connected to heart tissue, said system comprising:

an intracardiac electrogram signal receiver receiving intracardiac electrogram signals from the implantable medical device;

a programming operation signal receiver receiving signals from the implantable medical device representative of programming operations performed by the implantable medical device in response to programming signals received by the implantable medical device;

an icon generator generating icons representative of programming operations performed within the implantable medical device in response to programming signals received by the implantable medical device; and a graphic display displaying intracardiac electrogram signals received from the implantable medical device along with icons representative of programming operations performed by the implantable medical device in response to programming signals received by the implantable medical device.

34. A system for detecting and displaying information received from an implantable medical device, said system comprising:

an intracardiac electrogram signal receiver receiving intracardiac electrogram signals from the implantable medical device;

a programming operation signal receiver receiving signals from the implantable medical device representative of operations performed by the implantable medical device in response to conditions sensed by the implantable medical device;

an icon generator generating icons representative of programming operations performed within the implantable medical device in response to conditions sensed by the implantable medical device; and a graphic display displaying intracardiac electrogram signals along with icons representative of operations performed by the implantable medical device in response to conditions sensed by the implantable medical device.

* * * * *